(12) United States Patent
Brady et al.

(10) Patent No.: US 7,780,693 B2
(45) Date of Patent: Aug. 24, 2010

(54) CATHETER

(75) Inventors: Eamon Brady, Elphin (IE); John Neilan, Gort (IE); David Vale, Clontarf (IE)

(73) Assignee: Salviac Limited, Dublin (IE)

( * ) Notice: Subject to any disclaimer, the term of this patent is extended or adjusted under 35 U.S.C. 154(b) by 0 days.

(21) Appl. No.: 10/180,980

(22) Filed: Jun. 27, 2002

(65) Prior Publication Data

US 2003/0093106 A1  May 15, 2003

Related U.S. Application Data

(60) Provisional application No. 60/301,820, filed on Jul. 2, 2001, provisional application No. 60/341,276, filed on Dec. 20, 2001.

(30) Foreign Application Priority Data

Jun. 27, 2001 (IE) ................ 2001/0591
Dec. 20, 2001 (IE) ................ 2001/1098

(51) Int. Cl.
*A61M 29/00* (2006.01)
(52) U.S. Cl. .................................. 606/200
(58) Field of Classification Search ............. 606/108, 606/200, 107, 194; 623/1.12, 1.11; 604/104–107
See application file for complete search history.

(56) References Cited

U.S. PATENT DOCUMENTS

| 5,040,548 A | 8/1991 | Yock |
| 5,147,379 A | 9/1992 | Sabbaghian et al. |
| 5,201,757 A | 4/1993 | Heyn et al. |
| 5,224,953 A * | 7/1993 | Morgentaler ................ 606/192 |
| 5,350,395 A | 9/1994 | Yock |
| 5,360,401 A | 11/1994 | Turnland et al. |

(Continued)

FOREIGN PATENT DOCUMENTS

EP   819411 A2   1/1998

(Continued)

OTHER PUBLICATIONS

US 6,348,062, 02/2002, Hopkins et al. (withdrawn)

*Primary Examiner*—Anhtuan T Nguyen
*Assistant Examiner*—Elizabeth Houston
(74) *Attorney, Agent, or Firm*—Sughrue Mion, PLLC; Jonathan Feuchtwang

(57) ABSTRACT

A delivery catheter 200 for rapid exchange delivery of an embolic protection filter 301 over a guidewire 22, and rapid exchange deployment of the filter 301 at a desired site in a vasculature. The delivery catheter 200 comprises a catheter body 2, a restraining sheath 10 and an elongate pull wire 9. The catheter body 2 comprises a proximal hypotube portion 5 and a radially offset distal spring pusher 6. The restraining sheath 10 is movable in a sliding manner relative to the catheter body 2 upon retraction of the wire 9, and the distal end of the pusher 6 is engageable with the filter 301 in a reception space 11 upon retraction of the sheath 10 to deploy the filter 301 out of the reception space 11. The pusher 6 has a guidewire lumen 16 and a proximal guidewire opening 17 for passage of the guidewire 22 through the lumen 16 and out through the proximal guidewire opening 17 in a rapid exchange manner.

64 Claims, 24 Drawing Sheets

U.S. PATENT DOCUMENTS

| | | | |
|---|---|---|---|
| 5,445,646 A | 8/1995 | Euteneuer et al. | |
| 5,451,233 A | 9/1995 | Yock | |
| 5,534,007 A | 7/1996 | St. Germain et al. | |
| 5,571,135 A * | 11/1996 | Fraser et al. | 623/1.12 |
| 5,593,418 A * | 1/1997 | Mollenauer | 606/192 |
| 5,649,953 A * | 7/1997 | Lefebvre | 606/200 |
| 5,662,703 A * | 9/1997 | Yurek et al. | 623/1.12 |
| 5,690,644 A | 11/1997 | Yurek et al. | |
| 5,738,667 A | 4/1998 | Solar | |
| 5,776,141 A * | 7/1998 | Klein et al. | 623/1.11 |
| 5,817,101 A | 10/1998 | Fiedler | |
| 5,968,052 A | 10/1999 | Sullivan, III et al. | |
| 5,993,460 A | 11/1999 | Beitelia et al. | |
| 6,042,588 A | 3/2000 | Munsinger et al. | |
| 6,113,608 A | 9/2000 | Monroe et al. | |
| 6,117,140 A | 9/2000 | Munsinger | |
| 6,120,522 A | 9/2000 | Vrba et al. | |
| 6,142,987 A | 11/2000 | Tsugita | |
| 6,146,389 A * | 11/2000 | Geitz | 606/108 |
| 6,146,415 A | 11/2000 | Fitz | |
| 6,165,167 A | 12/2000 | Delaloye | |
| 6,165,197 A | 12/2000 | Yock | |
| 6,171,327 B1 | 1/2001 | Daniel et al. | |
| 6,174,327 B1 | 1/2001 | Mertens et al. | |
| 6,228,110 B1 | 5/2001 | Munsinger | |
| 6,238,410 B1 | 5/2001 | Vrba et al. | |
| 6,254,628 B1 * | 7/2001 | Wallace et al. | 623/1.12 |
| 6,290,710 B1 * | 9/2001 | Cryer et al. | 606/200 |
| 6,346,116 B1 | 2/2002 | Brooks et al. | |
| 6,380,457 B1 | 4/2002 | Yurek et al. | |
| 6,391,044 B1 | 5/2002 | Yadav et al. | |
| 6,391,050 B1 * | 5/2002 | Broome | 623/1.11 |
| 6,443,971 B1 * | 9/2002 | Boylan et al. | 606/200 |
| 6,447,540 B1 * | 9/2002 | Fontaine et al. | 623/1.12 |
| 6,485,501 B1 | 11/2002 | Green | |
| 6,527,746 B1 * | 3/2003 | Oslund et al. | 604/160 |
| 6,530,939 B1 | 3/2003 | Hopkins et al. | |
| 6,537,294 B1 * | 3/2003 | Boyle et al. | 606/200 |
| 6,537,295 B2 * | 3/2003 | Petersen | 606/200 |
| 6,540,768 B1 | 4/2003 | Diaz et al. | |
| 6,544,279 B1 | 4/2003 | Hopkins et al. | |
| 6,613,075 B1 | 9/2003 | Healy et al. | |
| 6,616,679 B1 | 9/2003 | Khosravi et al. | |
| 6,616,680 B1 | 9/2003 | Thielen | |
| 6,616,681 B2 | 9/2003 | Hanson et al. | |
| 6,755,846 B1 * | 6/2004 | Yadav | 606/200 |
| 6,893,451 B2 * | 5/2005 | Cano et al. | 606/200 |
| 2001/0007947 A1 | 7/2001 | Kanesaka | |
| 2002/0004667 A1 | 1/2002 | Adams et al. | |
| 2002/0032461 A1 | 3/2002 | Marshall | |
| 2002/0042626 A1 | 4/2002 | Hanson et al. | |
| 2002/0082525 A1 | 6/2002 | Oslund et al. | |
| 2002/0083826 A1 | 7/2002 | Arshad et al. | |
| 2002/0095141 A1 | 7/2002 | Belef et al. | |
| 2003/0153942 A1 | 8/2003 | Wang et al. | |
| 2004/0199240 A1 | 10/2004 | Dorn | |

FOREIGN PATENT DOCUMENTS

| | | |
|---|---|---|
| JP | 2000-504263 A | 4/2000 |
| JP | 2000-245846 A | 9/2000 |
| WO | WO 98/12988 A1 | 4/1998 |
| WO | 98/33443 A1 | 6/1998 |
| WO | WO98/33443 * | 8/1998 |
| WO | WO 98/33443 A1 | 8/1998 |
| WO | WO 99/25280 A1 | 5/1999 |
| WO | WO 99/44541 A1 | 9/1999 |
| WO | WO 99/47075 A1 | 9/1999 |
| WO | WO 99/49808 A1 | 10/1999 |
| WO | WO 99/51167 A1 | 10/1999 |
| WO | WO 99/56801 A2 | 11/1999 |
| WO | WO 00/00104 A1 | 1/2000 |
| WO | WO 00/16705 A1 | 3/2000 |
| WO | WO 00/71059 A1 | 11/2000 |
| WO | WO 00/78248 A1 | 12/2000 |
| WO | WO 01/08743 A1 | 2/2001 |
| WO | WO 01/34061 A1 | 5/2001 |
| WO | WO 01/66178 A1 | 9/2001 |
| WO | WO 01/80776 | 11/2001 |
| WO | WO 01/80777 A2 | 11/2001 |
| WO | WO 02/28292 | 4/2002 |
| WO | 03/002019 A2 | 1/2003 |

\* cited by examiner

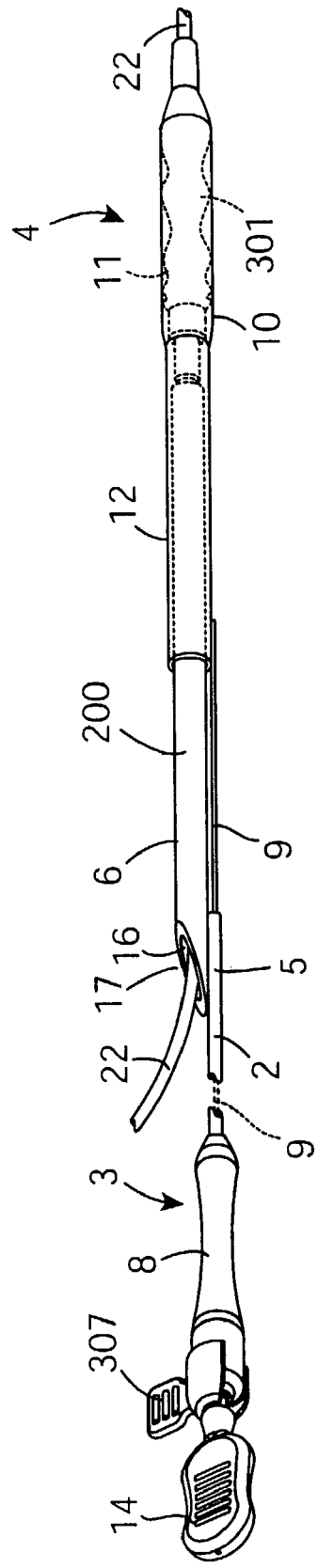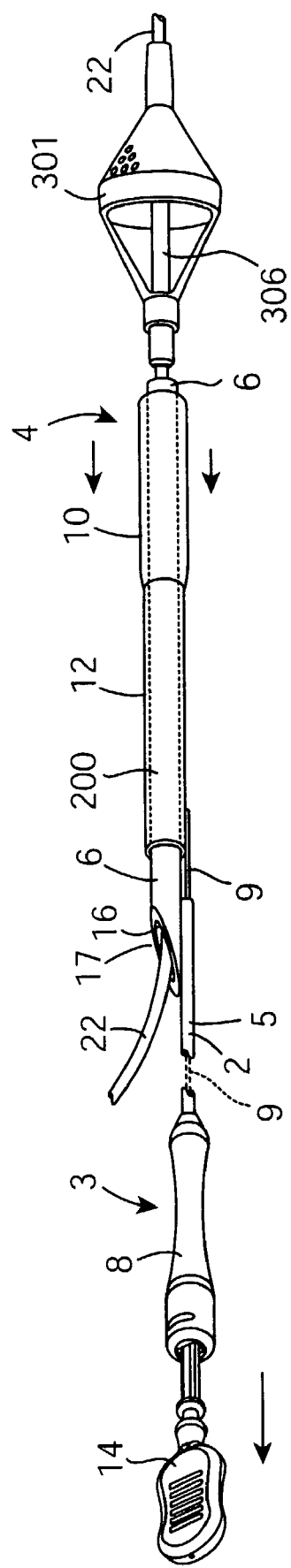

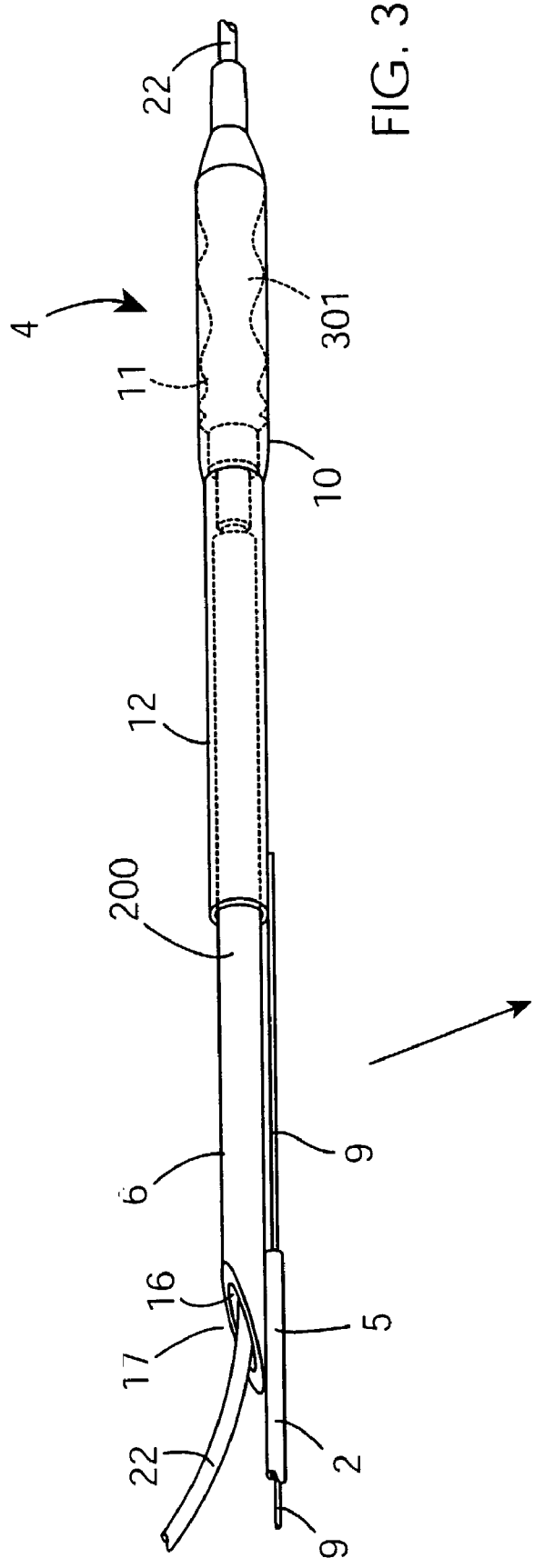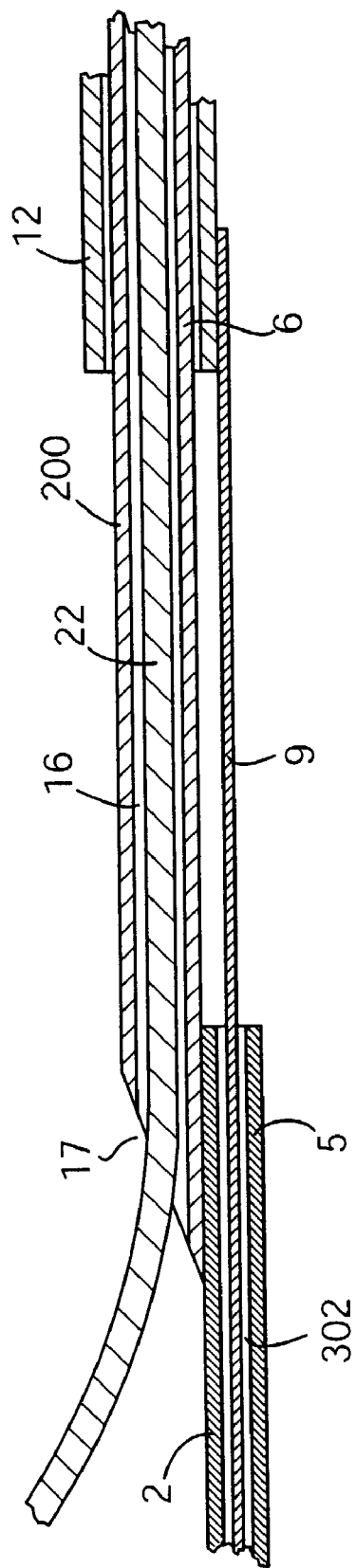

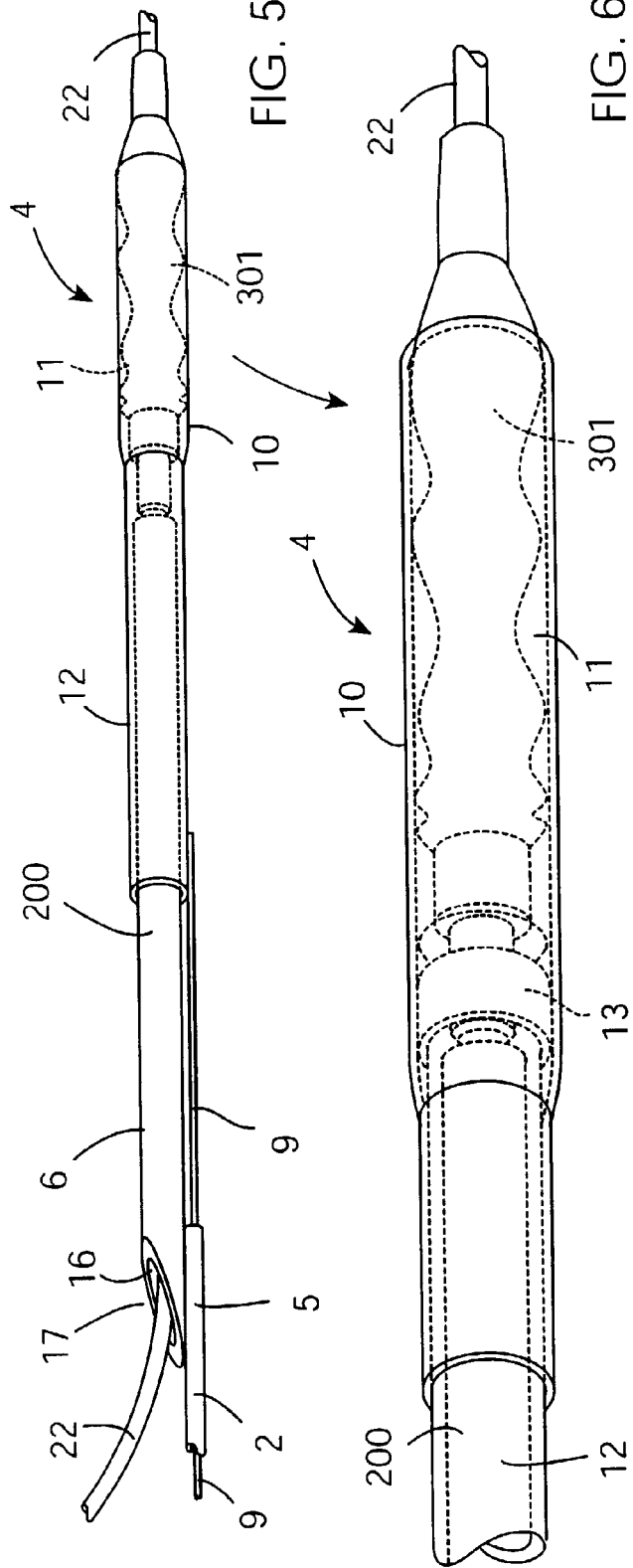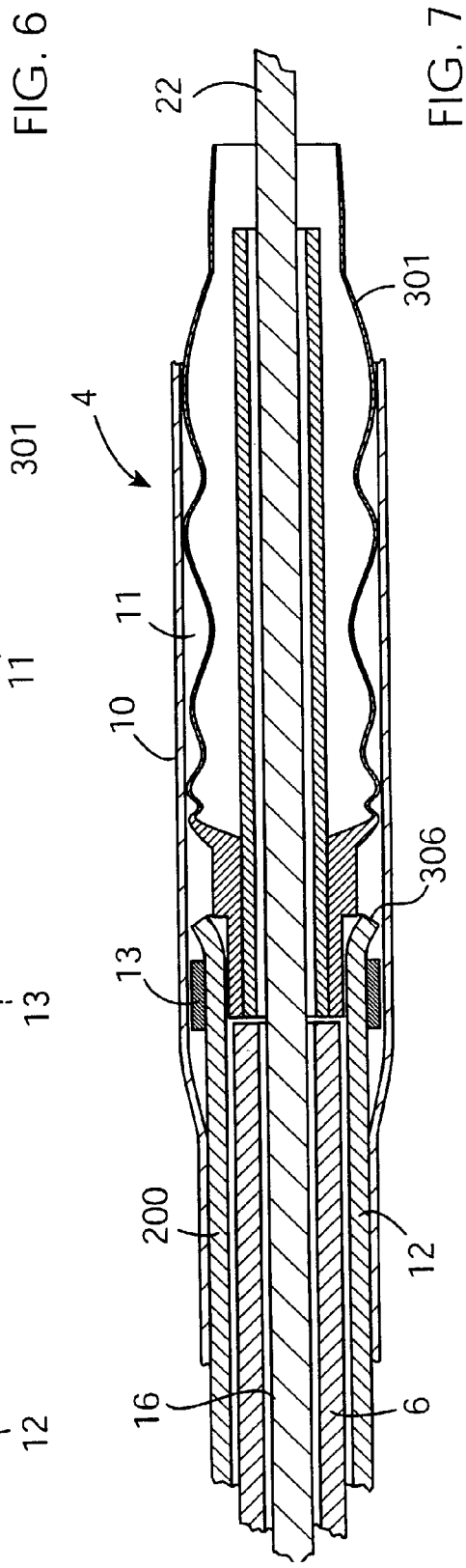

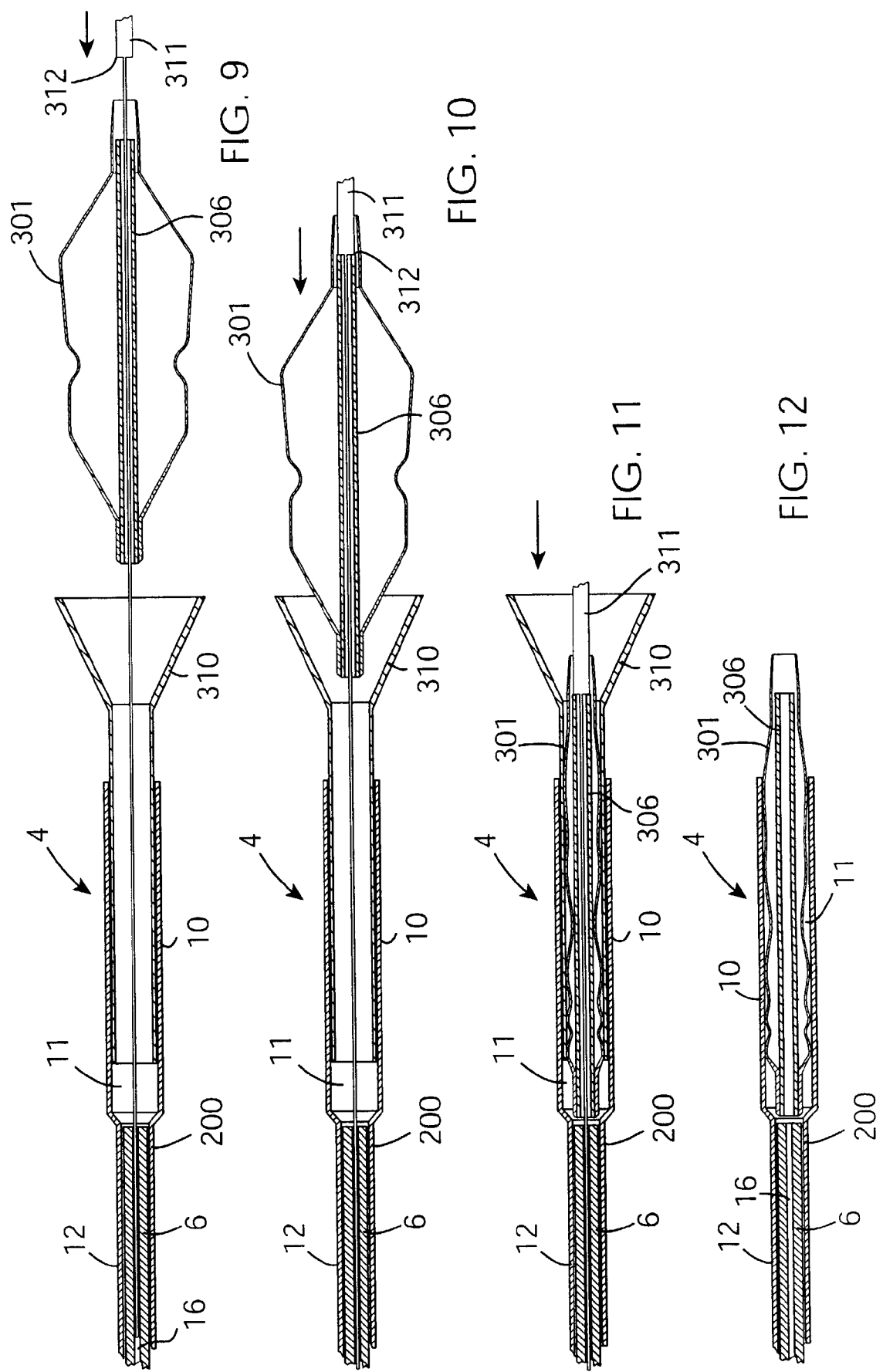

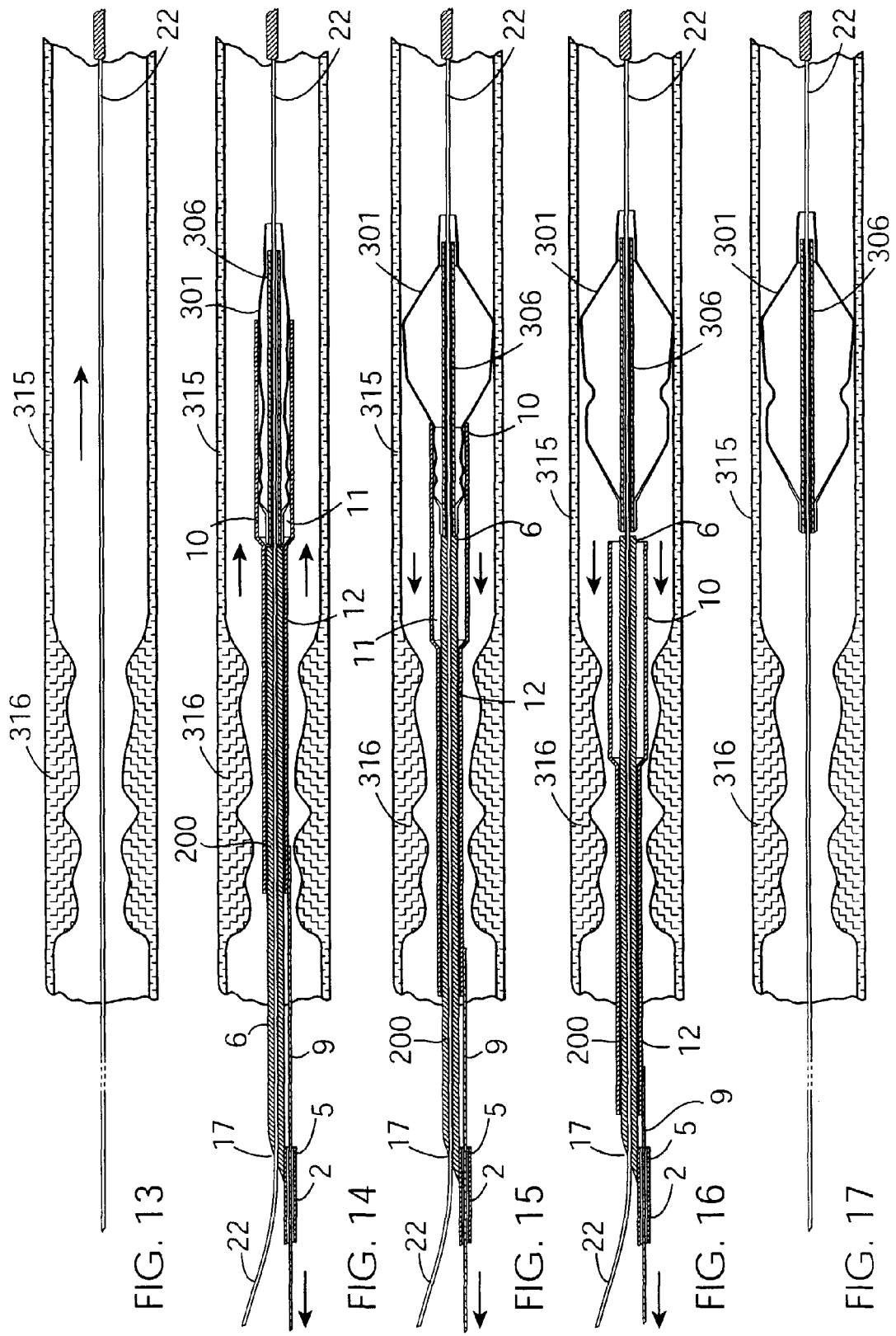

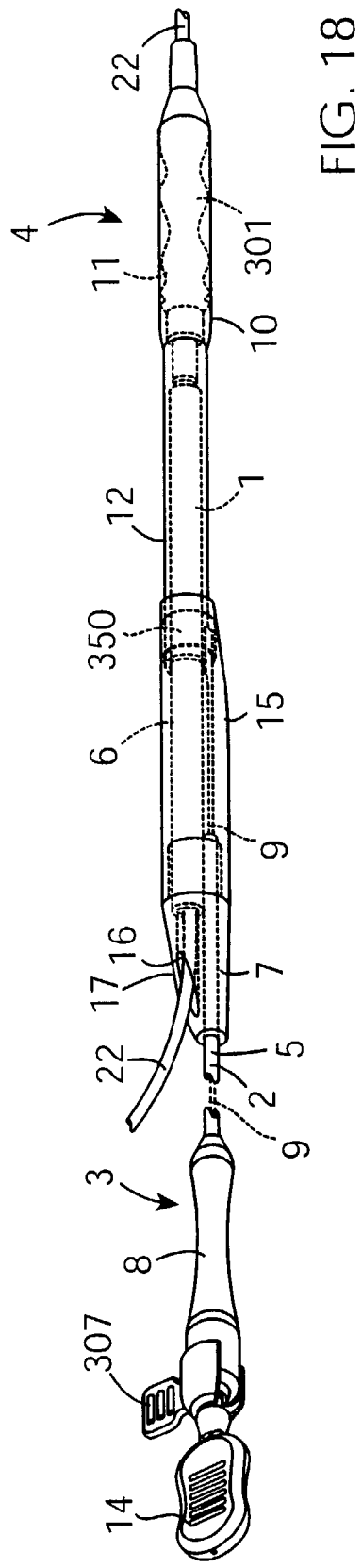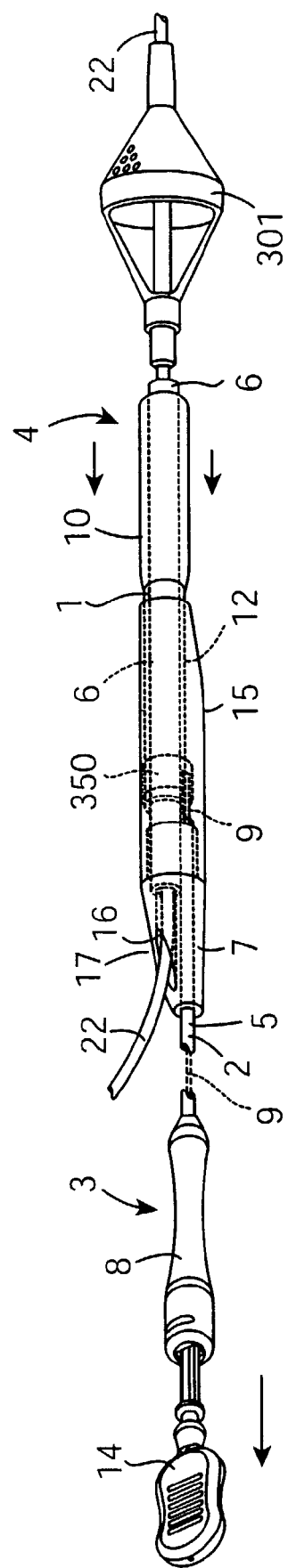

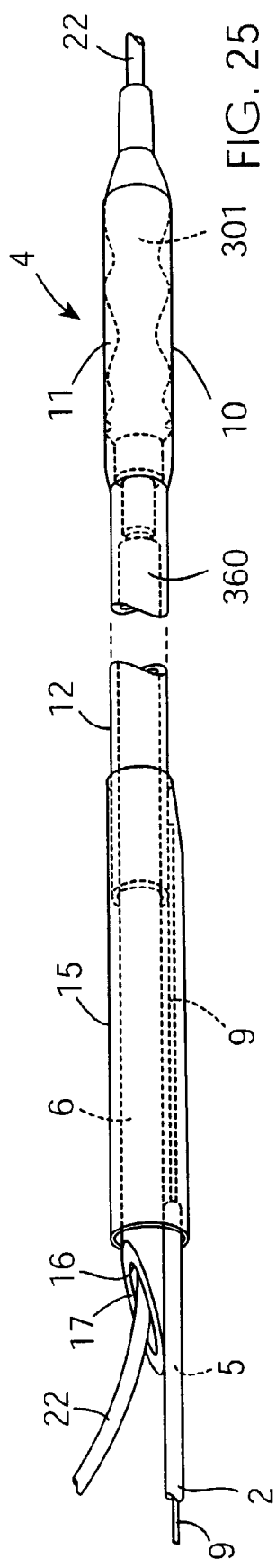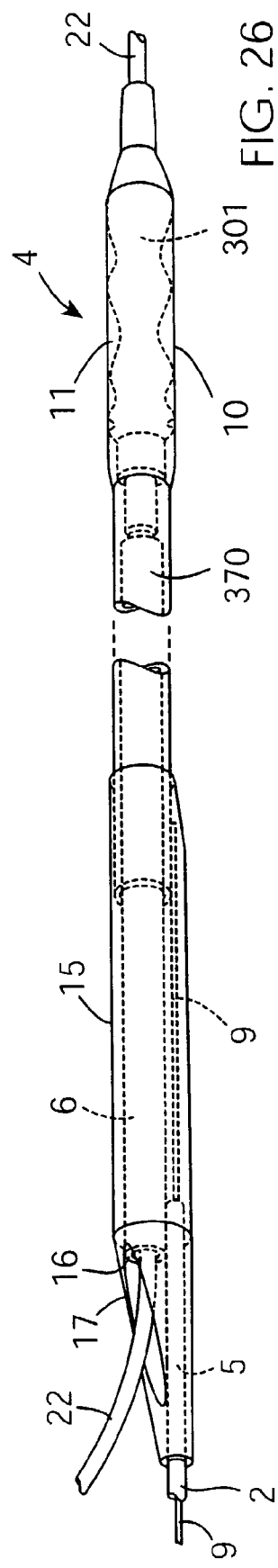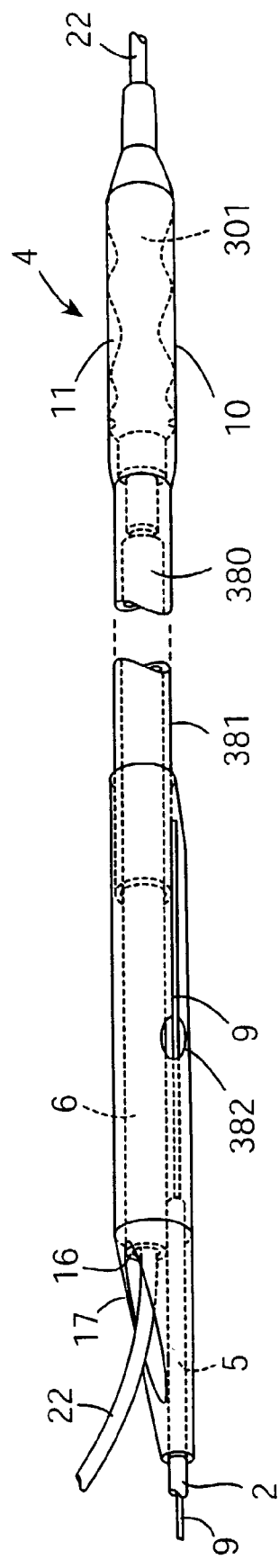

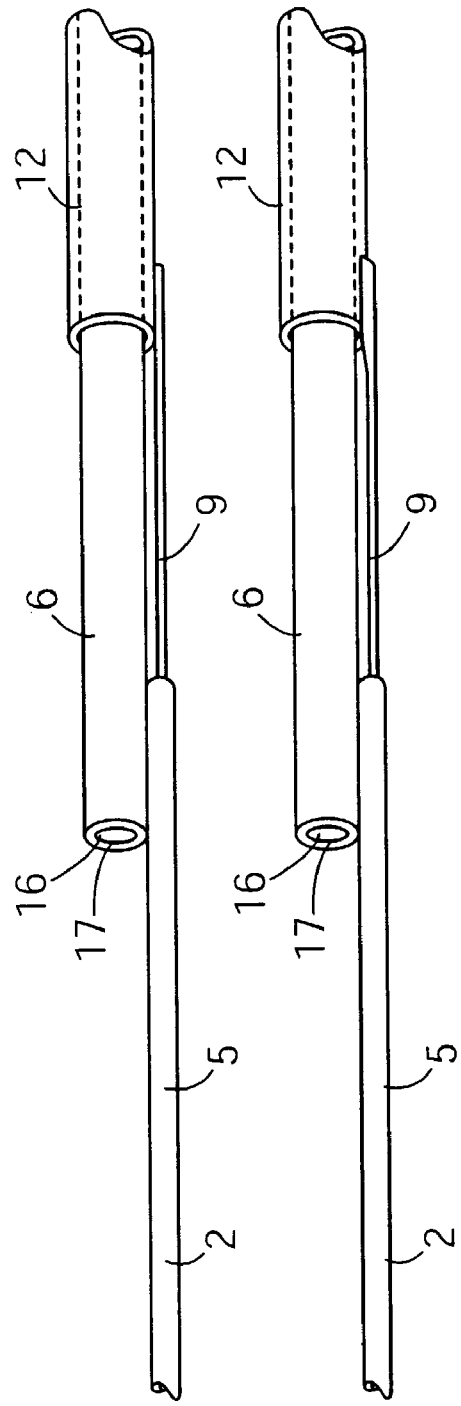

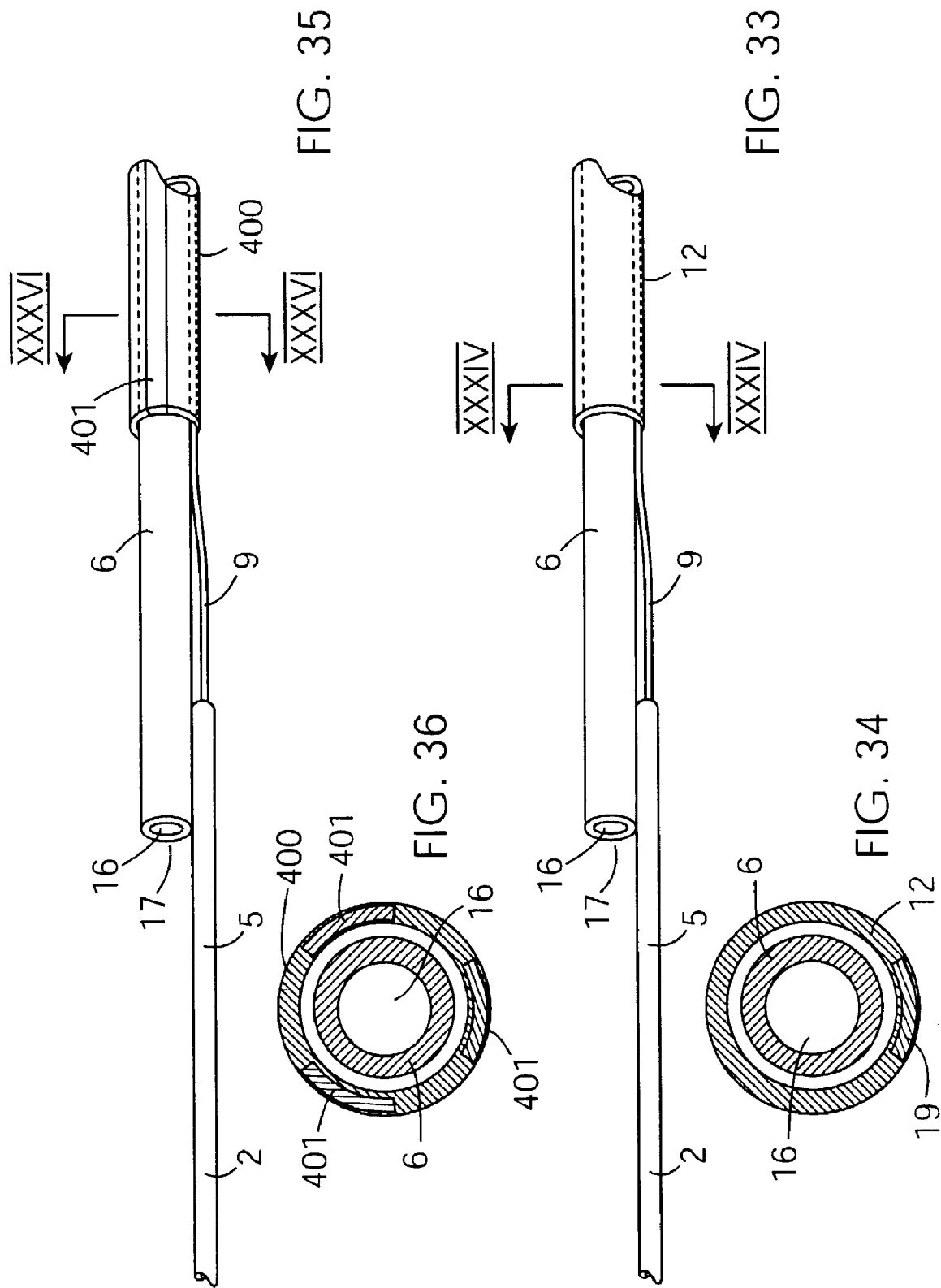

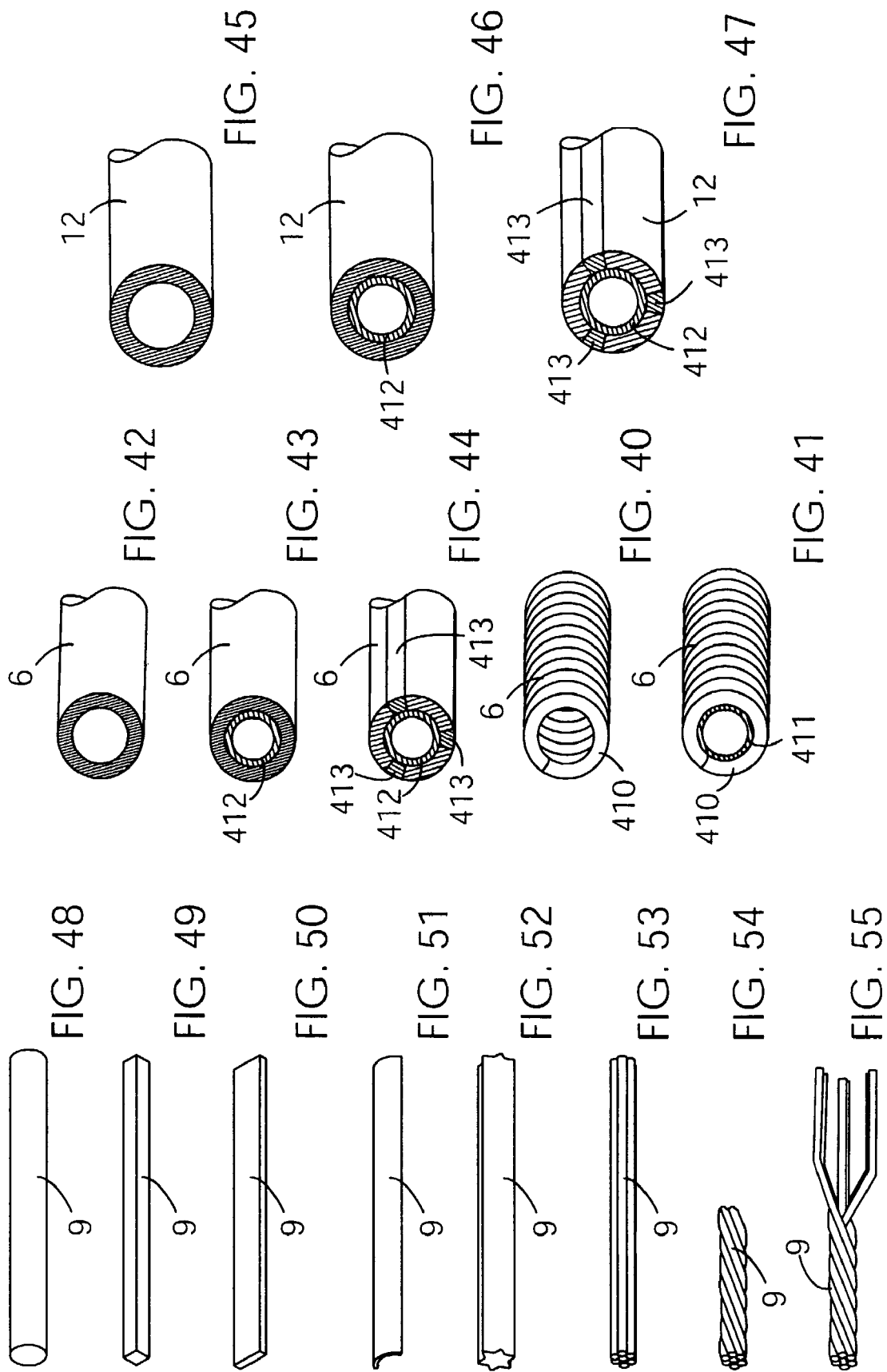

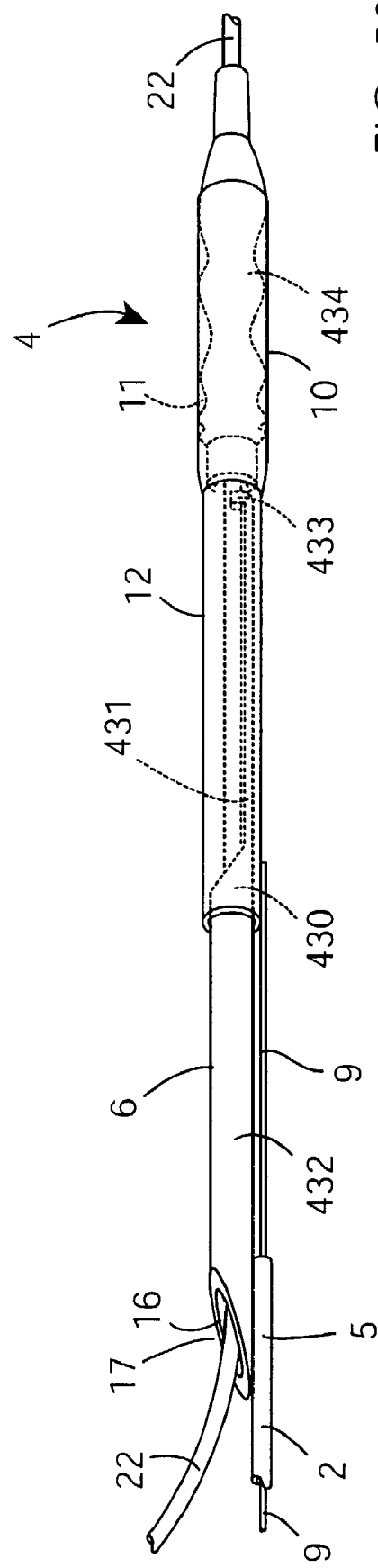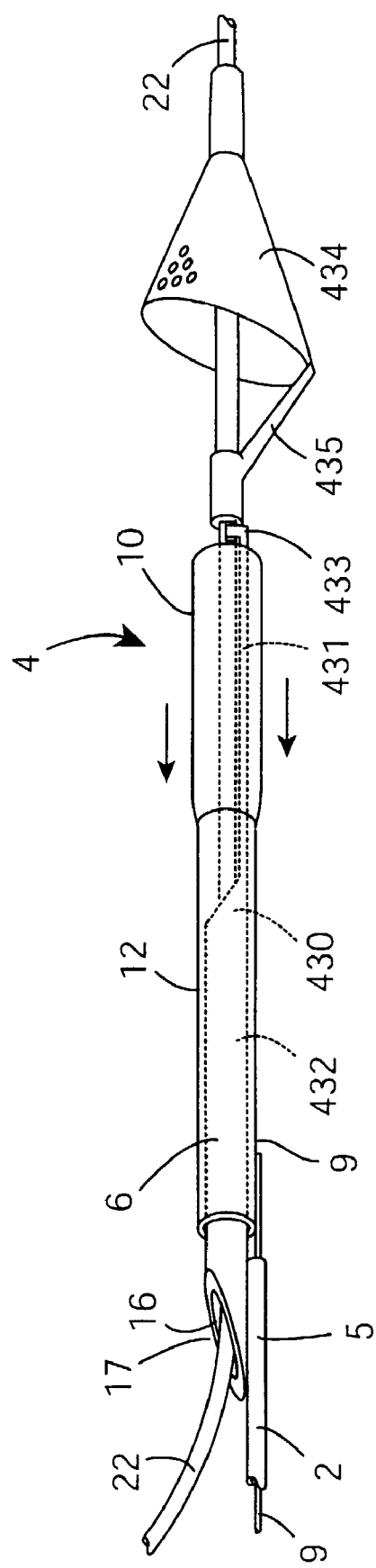

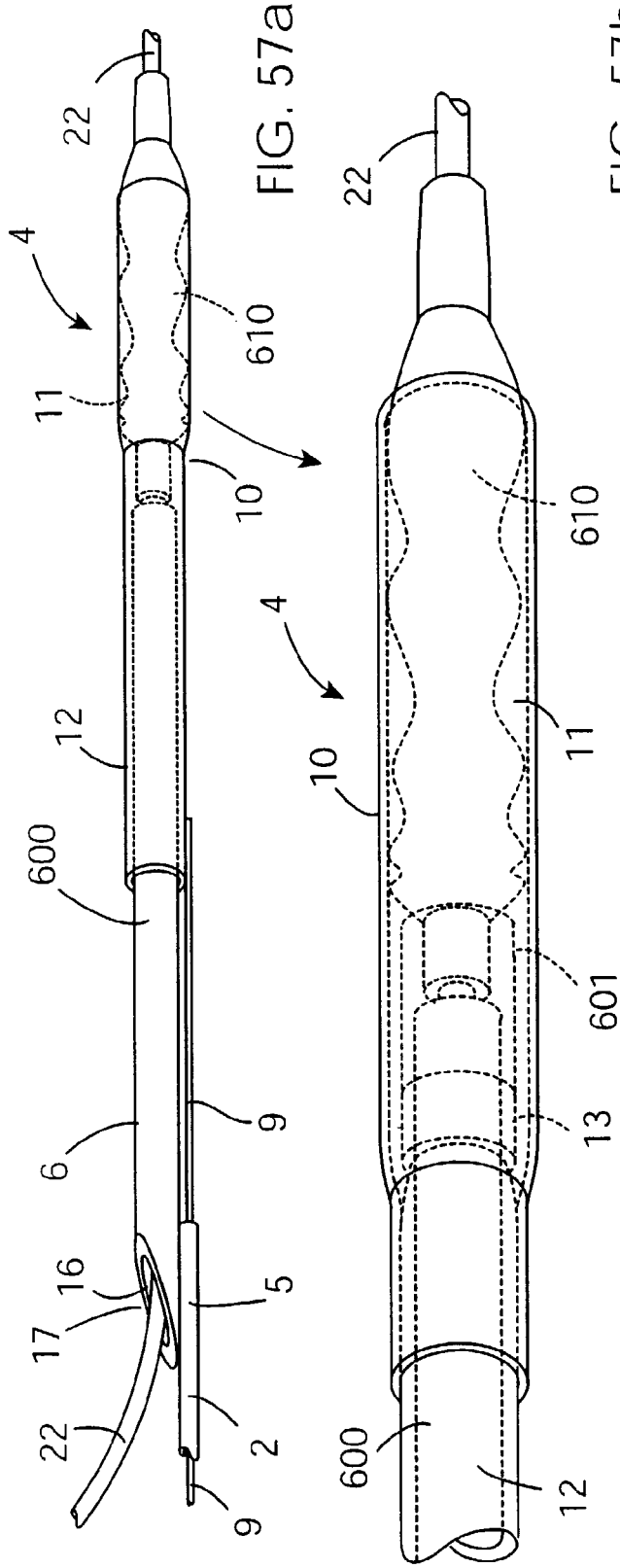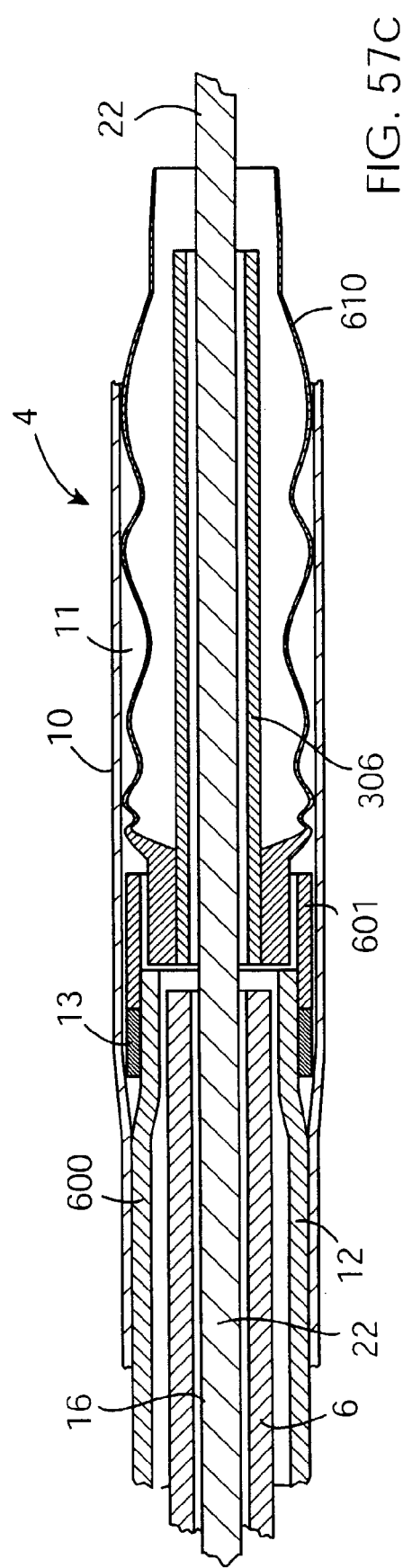

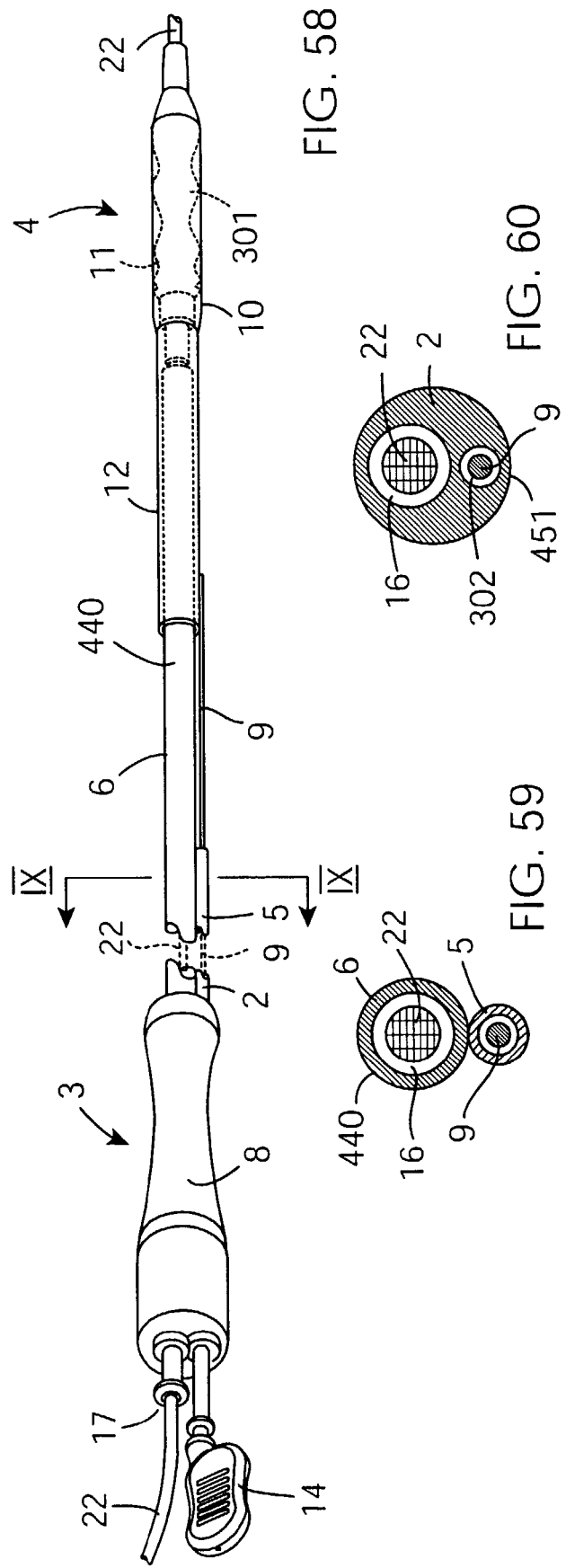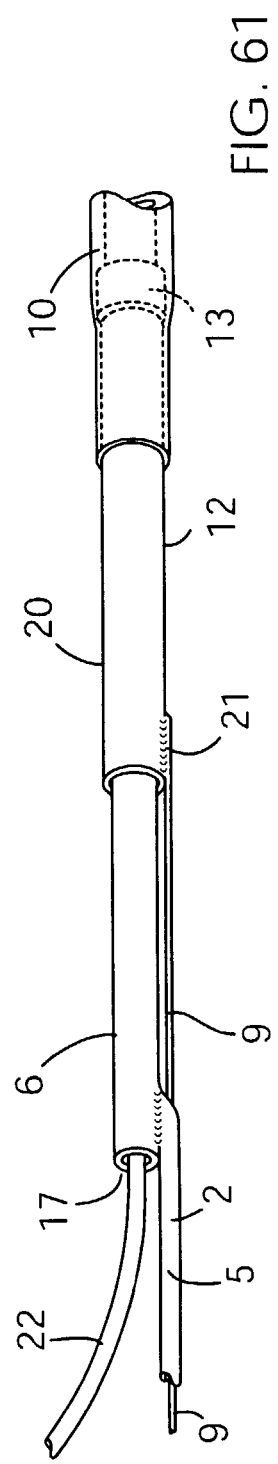

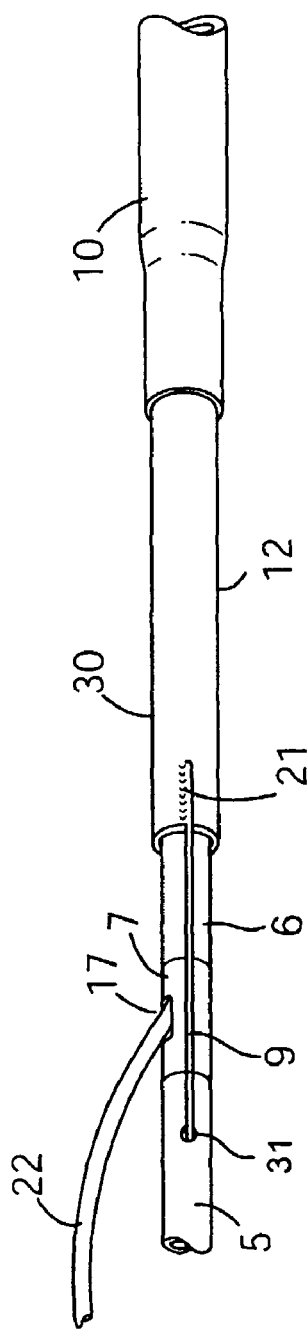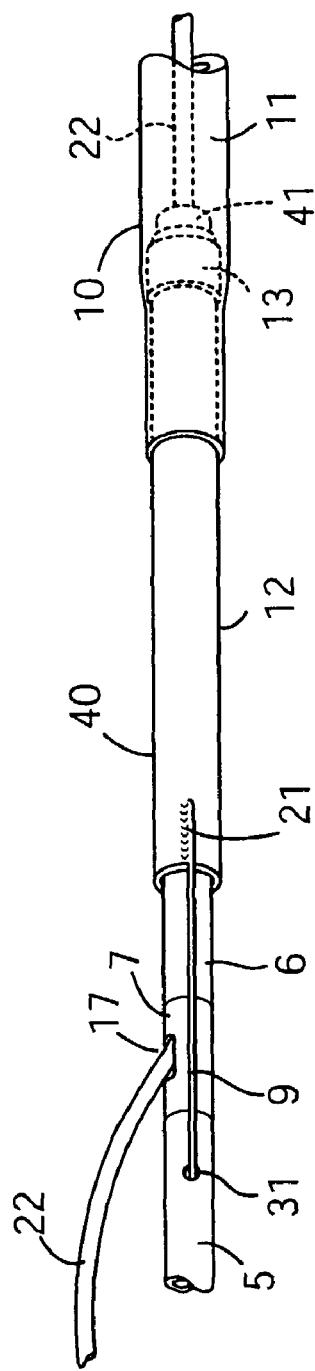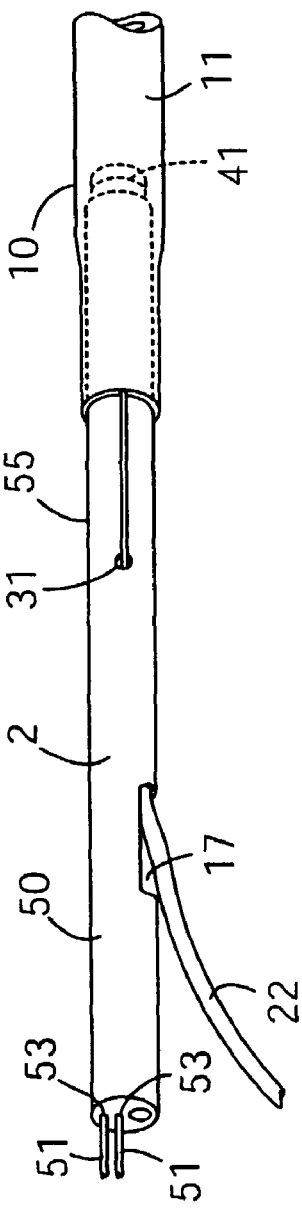

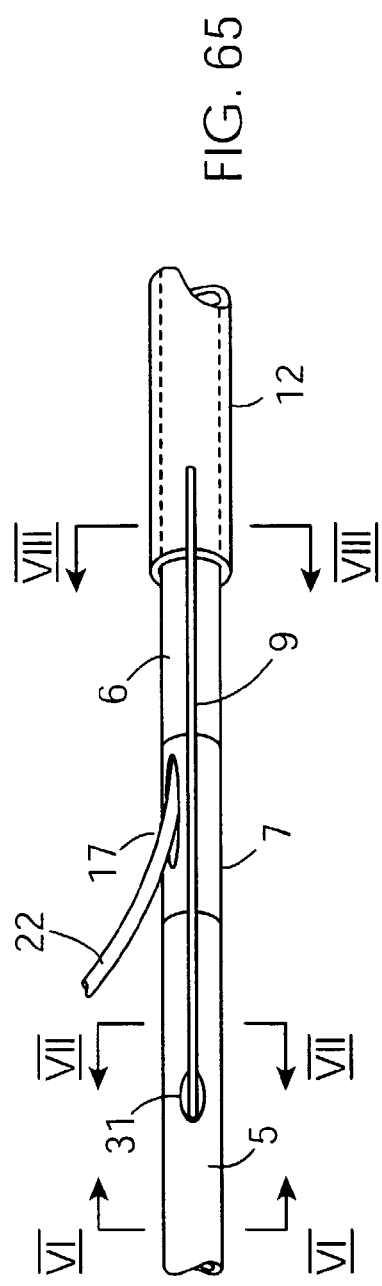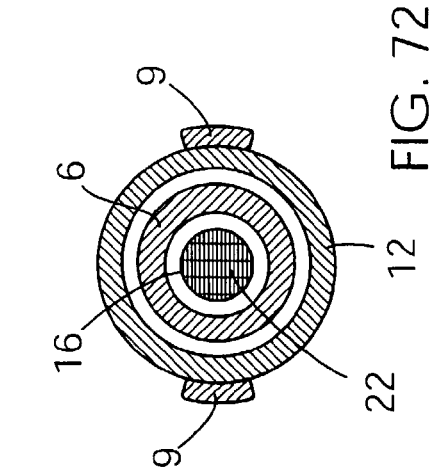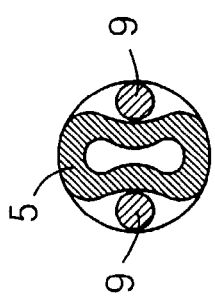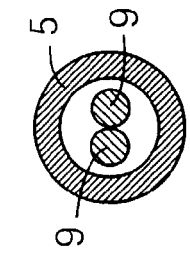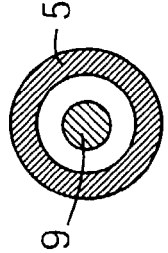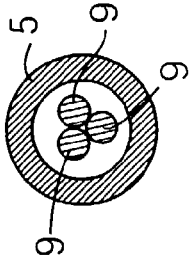

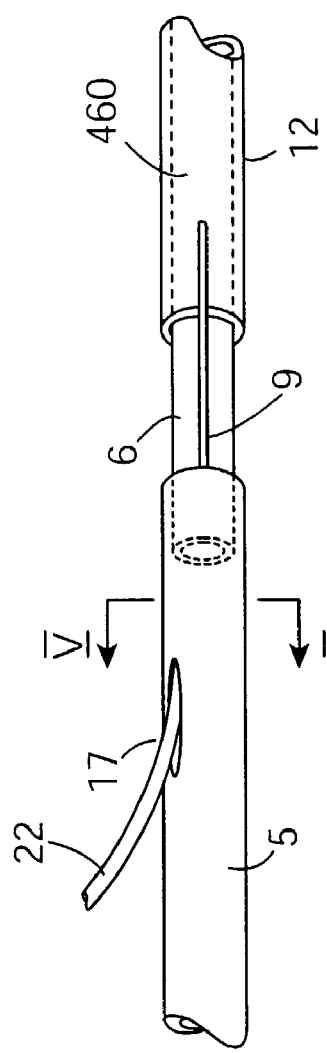
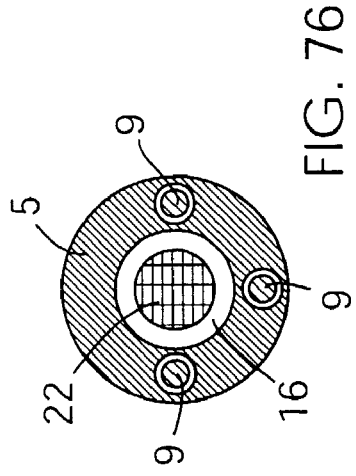
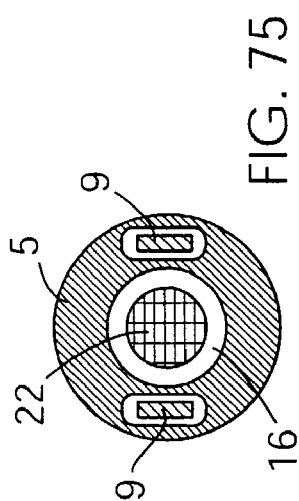
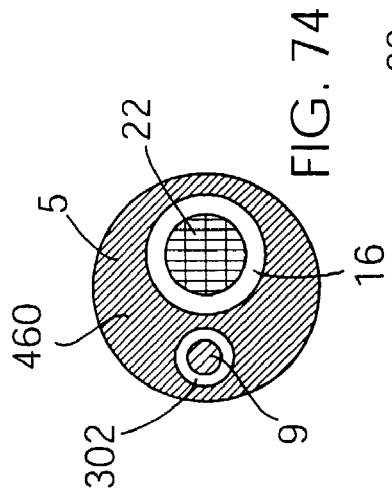
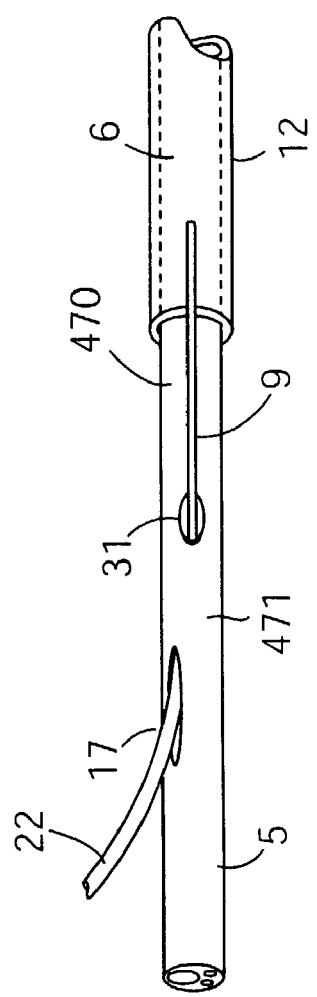

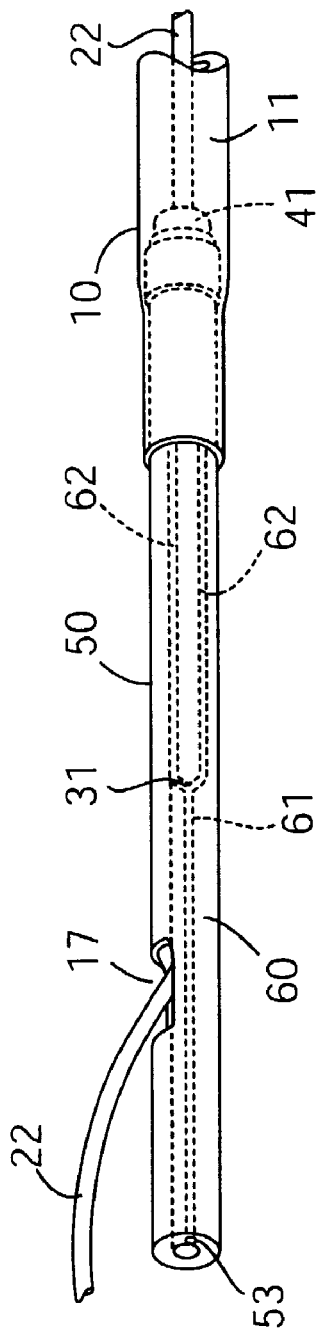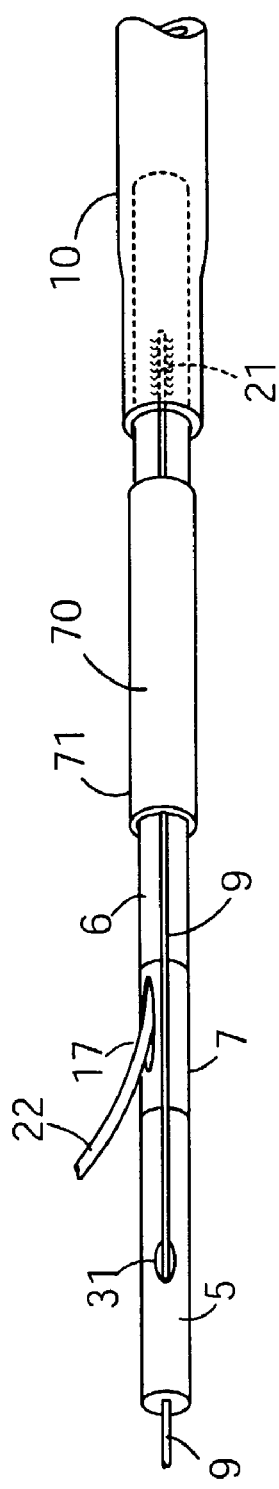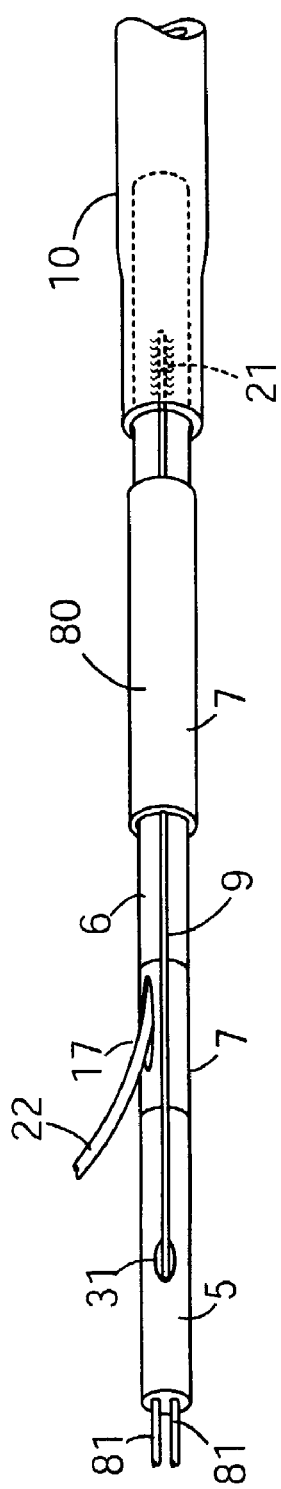

CATHETER

CROSS REFERENCE TO RELATED APPLICATION

This application is related to, and claims the benefit of, the following patent applications, namely: Irish Patent Application No. 2001/0591, filed Jun. 27, 2001; U.S. Patent Application No. 60/301,820, filed Jul. 2, 2001; Irish Patent Application No. 2001/1098, filed Dec. 20, 2001; and U.S. Patent Application No. 60/341,276, filed Dec. 20, 2001; all of which are hereby incorporated by reference in their entirety.

FIELD OF THE INVENTION

This invention relates to a delivery catheter for delivering an embolic protection filter to a desired site in a vasculature, and for deploying the filter at the desired site. In particular this invention relates to a delivery catheter, which is configured to facilitate rapid exchange of the catheter over a guidewire during both delivery and deployment of the filter.

Exchange of a catheter over a guidewire using a rapid exchange arrangement enables an interventional procedure to be performed by a single operator in a fast, efficient manner.

This invention is aimed at providing a catheter which will facilitate both delivery and deployment of an embolic protection filter.

SUMMARY OF THE INVENTION

According to the invention there is provided a delivery catheter comprising:

a catheter shaft having a control lumen for an operating element;

a pod defining a reception space for an embolic protection filter, the pod being movable relative to the catheter shaft upon operation of the operating element to facilitate deployment of a filter from within the reception space; and an engagement element for engaging a filter in the reception space upon movement of the pod relative to the catheter shaft.

In one embodiment of the invention a distal end of the catheter shaft is disconnected from a proximal end of the pod for movement of the pod relative to the catheter shaft. The distal end of the catheter shaft is preferably spaced proximally of the proximal end of the pod. The catheter may comprise a covering sleeve extending between the distal end of the catheter shaft and the proximal end of the pod. In one case the covering sleeve is mounted to the catheter shaft. Ideally the pod is movable relative to the covering sleeve. In another case the covering sleeve is mounted to the pod. Ideally the covering sleeve is movable relative to the catheter shaft.

In another embodiment of the invention the engagement element is attached to the catheter shaft.

The engagement element may extend distally of the catheter shaft.

In one case the engagement element comprises a pusher. Preferably the pusher comprises a coiled spring. The pusher may be of a high modulus of elasticity polymeric material.

In one embodiment the engagement element defines a guidewire lumen therethrough. Preferably the engagement element has a guidewire opening at a proximal end of the guidewire lumen. Ideally the engagement element is configured for passage of a guidewire from the guidewire lumen through the guidewire opening substantially parallel to the longitudinal axis of the catheter shaft. Most preferably the longitudinal axis of the engagement element is substantially parallel to the longitudinal axis of the catheter shaft at least in the region of the guidewire opening. The guidewire opening may face proximally.

In a preferred case the guidewire opening is located a substantial distance distally of a proximal end of the catheter for rapid exchange of the catheter over a guidewire.

In a further embodiment of the invention the cross-sectional area of the operating element is small relative to the cross-sectional area of the catheter shaft along at least part of the length of the operating element. Preferably the cross-sectional area of the operating element is small relative to the cross-sectional area of the catheter shaft in the region of the guidewire opening.

Preferably in the delivery configuration the cross-sectional area of the operating element is small relative to the cross-sectional area of the catheter shaft for a distance of at least 10 mm proximally of the guidewire opening. Most preferably in the delivery configuration the cross-sectional area of the operating element is small relative to the cross-sectional area of the catheter shaft for a distance of at least 20 mm proximally of the guidewire opening. Ideally in the delivery configuration the cross-sectional area of the operating element is small relative to the cross sectional area of the catheter shaft for a distance of at least 30 mm proximally of the guidewire opening. Desirably in the delivery configuration the cross sectional area of the operating element is small relative to the cross-sectional area of the catheter shaft for a distance of at least 40 mm proximally of the guidewire opening.

In another embodiment the diameter of the operating element is in the range of from 0.008" to 0.015". Ideally the diameter of the operating element is in the range of from 0.01" to 0.012".

The operating element enables a user to achieve a steady, accurate deployment at a desired site in a vasculature while ensuring the overall crossing profile of the delivery catheter is kept to a minimum.

The operating element may comprise a control wire, in this case a pull wire. In addition during advancement of the catheter through a vasculature, the control wire may bend around its own neutral axis. This results in the contribution of the control wire to the overall stiffness of the catheter being kept to a minimum for a highly trackable delivery catheter.

The operating element may exit the control lumen at a location distally of the guidewire opening. The operating element may exit the control lumen at a location proximally of the guidewire opening. The operating element may exit the control lumen at a location adjacent the guidewire opening.

In another embodiment of the invention the catheter comprises means to guide passage of a guidewire through the guidewire opening. The means to guide passage may comprise a guide tube. Preferably the guide tube is located at the guidewire opening. The guide tube may be mounted to the engagement element.

In a preferred case the guidewire lumen of the engagement element is offset radially from the control lumen of the catheter shaft.

The catheter shaft may comprise a mounting piece for attaching the engagement element to the catheter shaft. In one case the distal end of the catheter shaft is located distally of the proximal end of the engagement element. Preferably the mounting piece is more flexible than the catheter shaft and the engagement element.

In another case the mounting piece is more stiff than the catheter shaft and the engagement element.

The mounting piece may taper proximally inwardly.

The mounting piece may taper distally inwardly.

In one embodiment the guidewire opening is provided by an opening in the mounting piece.

In a preferred case the engagement element comprises an engagement surface for engaging a filter in the reception space. Ideally the engagement surface is provided by a distal end face of the engagement element. The engagement surface may extend circumferentially around the engagement element to define an "O"-shape. The engagement surface may extend partially circumferentially around the engagement element to define an "U"-shape.

Ideally the engagement surface is configured to engage a tubular member of a filter. The tubular member preferably defines a guidewire lumen therethrough.

In one embodiment the operating element is attached to the pod. Preferably the operating element is attached to an exterior surface of the pod.

The pod may comprise a proximal portion and a distal portion, the distal portion defining the reception space. Ideally the operating element is attached to the proximal portion.

The proximal portion and the distal portion may be fixed together by means of a marker band.

In one embodiment the operating element is a control wire. Preferably the operating element is a pull wire.

The operating element may comprise a plurality of wires. Ideally the wires are braided together along at least part of the length of the operating element.

In a further case the stiffness of the catheter shaft decreases distally. Preferably the stiffness of the catheter shaft decreases from a point proximally of the guidewire opening to a point distally of the guidewire opening. Ideally the stiffness decreases in a gradual manner. Most preferably the catheter shaft includes at least one slot in the catheter shaft. The slot may extend along the catheter shaft in a spiral. Ideally the pitch of the spiral varies along the catheter shaft.

In another embodiment the pod is thin-walled. Ideally the pod has a wall thickness in the range of from 0.0005" to 0.00075". The pod may be of the material polyethyleneterephthalate or polytetrafluoroethylene.

In another aspect the invention provides a catheter comprising a proximal shaft portion and a distal shaft portion attached to the proximal shaft portion, and means to stiffen the catheter at the junction between the proximal shaft portion and the distal shaft portion.

In one embodiment the catheter comprises a mounting piece for attaching the distal shaft portion to the proximal shaft portion. Preferably the distal end of the proximal shaft portion is located distally of the proximal end of the distal shaft portion to stiffen the junction. Ideally the mounting piece is more flexible than the proximal shaft portion and the distal shaft portion.

In another case the mounting piece is more stiff than the proximal shaft portion and the distal shaft portion to stiffen the junction.

Ideally the catheter comprises strain relief means. The mounting piece may taper distally inwardly. The mounting piece may taper proximally inwardly.

In a further embodiment a guidewire opening is provided in the catheter, the guidewire opening being located a substantial distance distally of a proximal end of the catheter for rapid exchange of the catheter over a guidewire. Ideally the guidewire opening is provided by an opening in the mounting piece. Most preferably the guidewire opening faces in a direction substantially parallel to the longitudinal axis of the catheter.

The catheter may comprise means to guide passage of a guidewire through the guidewire opening in the catheter. Preferably the means to guide passage is provided by the mounting piece.

The invention also provides in a further aspect a delivery catheter comprising:

a catheter shaft;

a pod defining a reception space for an embolic protection filter; and an operating element coupled to the pod;

the pod being movable relative to the catheter shaft upon operation of the operating element to facilitate deployment of a filter from within the reception space;

the operating element being coupled to the exterior surface of the pod.

In one embodiment of the invention the operating element extends internally through a control lumen in the catheter shaft, exits the control lumen and extends externally along the pod.

Ideally the operating element is fixedly attached to the pod.

The operating element may be a control wire. Preferably the operating element is a pull wire.

In one case the pod comprises a proximal portion and a distal portion, the operating element being coupled to the proximal portion.

A guidewire opening may be provided in the catheter located a substantial distance distally of a proximal end of the catheter for rapid exchange of the catheter over a guidewire.

Desirably the catheter comprises an engagement element for engaging a filter in the reception space upon movement of the pod relative to the catheter shaft.

In another aspect of the invention there is provided a delivery catheter comprising:

a catheter shaft;

a pod defining a reception space for an embolic protection filter, the pod being movable relative to the catheter shaft to facilitate deployment of a filter from within the reception space; and an engagement element for engaging a filter in the reception space upon movement of the pod relative to the catheter shaft;

the engagement element being offset in the radial direction from the catheter shaft.

The engagement element may be attached to the catheter shaft.

Preferably the engagement element extends distally of the catheter shaft.

In one case the distal end of the catheter shaft is located distally of the proximal end of the engagement element.

In a further embodiment the catheter comprises a mounting piece for attaching the engagement element to the catheter shaft.

Ideally the catheter comprises an operating element coupled to the pod for moving the pod relative to the catheter shaft.

A guidewire opening may be provided in the catheter located a substantial distance distally of a proximal end of the catheter for rapid exchange of the catheter over a guidewire.

The delivery catheter of the invention is particularly suitable for delivering an embolic protection filter through a vasculature over a guidewire, and for deploying the filter at a desired site in the vasculature. In this case, the distal portion of the catheter body is thin-walled, for example with a wall thickness in the range of from 0.0005" to 0.00075". The distal portion is preferably of the material polyethyleneterephthalate (PET), or polytetrafluoroethylene (PTFE).

BRIEF DESCRIPTION OF THE DRAWINGS

The invention will be more clearly understood from the following description of some embodiments thereof, given by way of example only, with reference to the accompanying drawings, in which:

FIG. 1 is a partially cut-away, perspective view of a delivery catheter according to the invention passing over a guidewire;

FIG. 2 is a partially cut-away, perspective view of the catheter of FIG. 1, in use;

FIG. 3 is a partially cut-away, perspective view of a part of the catheter of FIG. 1;

FIG. 4 is an enlarged, cross-sectional, side view of a part of the catheter of FIG. 3;

FIG. 5 is a partially cut-away, perspective view of a part of the catheter of FIG. 1;

FIG. 6 is an enlarged, partially cut-away, perspective view of a part of the catheter of FIG. 5;

FIG. 7 is a cross-sectional, side view of the catheter of FIG. 6;

FIGS. 9 to 12 are cross-sectional, side views illustrating loading of an embolic protection filter into the catheter of FIG. 1;

FIGS. 13 to 17 are cross-sectional, side views of the catheter of FIG. 1, in use;

FIG. 18 is a partially cut-away, perspective view of another delivery catheter according to the invention passing over a guidewire;

FIG. 19 is a partially cut-away, perspective view of the catheter of FIG. 18, in use;

FIGS. 25 to 27 are partially cut-away, perspective views of other delivery catheters according to the invention passing over a guidewire;

FIGS. 28 to 33 are perspective views of a part of other delivery catheters according to the invention;

FIG. 34 is a view along line XXXIV-XXXIV in FIG. 33;

FIG. 35 is a perspective view of a part of a further delivery catheter according to the invention;

FIG. 36 is a view along line XXXVI-XXXVI in FIG. 35;

FIGS. 39 to 44 are perspective views of an engagement element part of delivery catheters according to the invention;

FIGS. 45 to 47 are perspective views of a covering sleeve part of delivery catheters according to the invention;

FIGS. 48 to 55 are perspective views of an operating element part of delivery catheters according to the invention;

FIG. 56 is a partially cut-away, perspective view of another delivery catheter according to the invention passing over a guidewire;

FIG. 57 is a partially cut-away, perspective view of the catheter of FIG. 56, in use;

FIG. 57(a) is a partially cut-away, perspective view of another delivery catheter according to the invention passing over a guidewire;

FIG. 57(b) is an enlarged, partially cut-away, perspective view of a part of the catheter of FIG. 57(a);

FIG. 57(c) is a cross-sectional, side view of the catheter of FIG. 57(b);

FIG. 58 is a partially cut-away, perspective view of another delivery catheter according to the invention passing over a guidewire;

FIG. 59 is a view along line IX-IX in FIG. 58;

FIG. 60 is a cross-sectional, end view of another delivery catheter according to the invention passing over a guidewire;

FIG. 61 is a perspective view of another delivery catheter according to the invention passing over a guidewire;

FIGS. 62 to 64 are perspective views of other delivery catheters according to the invention passing over a guidewire;

FIG. 65 is a perspective view of a further delivery catheter according to the invention passing over a guidewire;

FIG. 66 is a view along line VI-VI in FIG. 65;

FIGS. 67 to 69 are cross-sectional, end views of other delivery catheters according to the invention;

FIG. 70 is a view along line VII-VII in FIG. 65;

FIG. 71 is a cross-sectional, end view of another delivery catheter according to the invention;

FIG. 72 is a view along line VIII-VIII in FIG. 65;

FIG. 73 is a perspective view of another delivery catheter according to the invention passing over a guidewire;

FIG. 74 is a view along line V-V in FIG. 73;

FIGS. 75 and 76 are cross-sectional, end views of other delivery catheters according to the invention passing over a guidewire;

FIG. 77 is a perspective view of a further delivery catheter according to the invention passing over a guidewire;

FIG. 78 is a partially cut-away, perspective view of another delivery catheter according to the invention passing over a guidewire;

FIGS. 79 to 81 are perspective views of further delivery catheters according to the invention passing over a guidewire;

DETAILED DESCRIPTION

Figure 8:
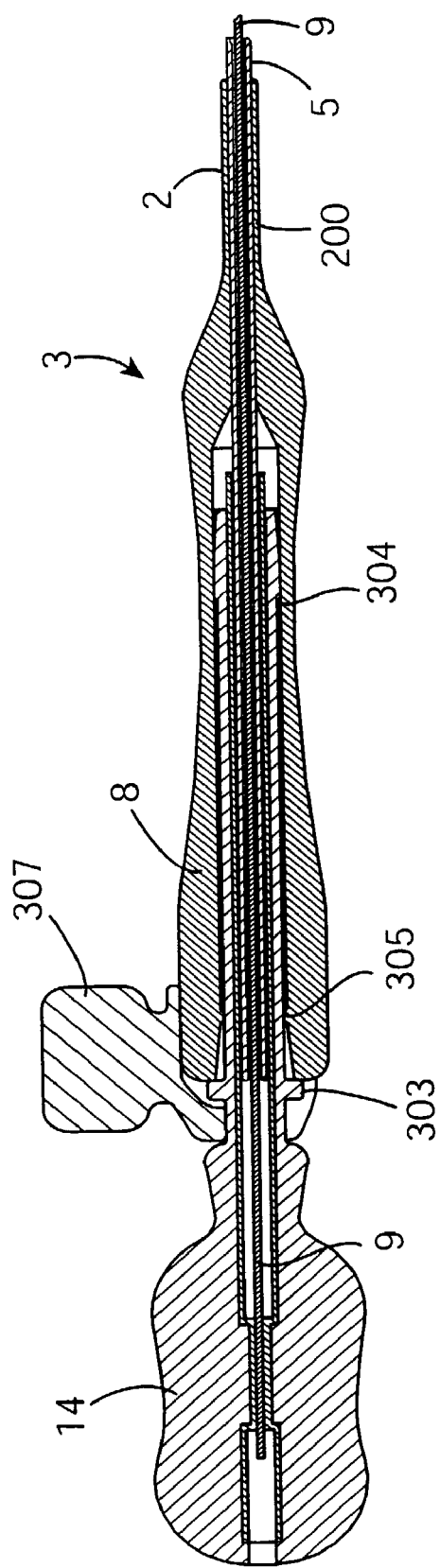
FIG. 8 is a cross-sectional, side view of a part of the catheter of FIG. 1.

Referring to the drawings, there is illustrated a delivery catheter according to the invention for delivery of an embolic protection filter through a vasculature over a guidewire, and deployment of the filter at a desired site in the vasculature.

The delivery catheter is suitable for rapid exchange over a guidewire during delivery and deployment of an embolic protection filter in a vasculature, and during withdrawal of the delivery catheter after deployment. In particular, the delivery catheter comprises a catheter body which extends between a proximal end and a distal end, and the catheter body defines an opening in a sidewall of the catheter body, and an opening at the distal end of the catheter body. A guidewire lumen extends between these openings to enable passage of a guidewire through the lumen, and thereby facilitate rapid exchange of the delivery catheter over the guidewire.

A distal portion of the catheter body defines a reception space for an embolic protection filter during delivery of the filter through a vasculature, and at least one elongate actuator is provided extending along the catheter body to facilitate deployment of the filter from within the reception space.

The delivery catheter is particularly suitable for delivery and deployment of a filter, which is received within the reception space but is separate and independent of the delivery catheter, and which is separate and independent of the rapid exchange guidewire. One example of this type of filter is the embolic protection filter described in International patent application number PCT/IE01/00053, the relevant contents of which are incorporated herein by reference.

In the region adjacent the guidewire opening in the sidewall of the catheter body, the actuator has a small cross-sectional area relative to the overall cross-sectional area of the delivery catheter. By providing such a thin, elongate actuator, this ensures that the guidewire opening in the sidewall of the catheter body, which serves as the rapid exchange port for a guidewire, will not be obstructed or occluded by manipulation of the actuator upon deployment of a filter from within the reception space.

The delivery catheter according to the invention is particularly suitable for delivery and deployment of an expandable embolic protection filter. In this case, the distal portion of the catheter body is provided by a sheath which restrains the embolic protection filter in a low-profile, collapsed configuration within the reception space during delivery to a desired site in a vasculature. The sheath is preferably thin-walled to minimise the overall crossing profile of the delivery catheter, especially during delivery of the embolic protection filter.

Referring to FIG. 1 to 17 there is illustrated a delivery catheter 200 according to the invention. The delivery catheter 200 comprises a catheter body 2 which extends between a proximal end 3 and a distal end 4, a restraining sheath 10 at the distal end 4 of the catheter body 2, and an elongate actuator, which is provided in this case in the form of a stainless steel wire 9.

The catheter body 2 comprises a proximal hypotube portion 5 and a radially offset distal spring pusher 6. As illustrated in FIGS. 3 and 4, the pusher 6 is fixedly attached to the hypotube 5 in a side-by-side overlapping arrangement with the proximal end of the pusher 6 located proximally of the distal end of the hypotube 5.

The pusher 6 has a guidewire lumen 16 extending through the pusher 6 with an opening 17 at the proximal end of the lumen 16 for passage of a guidewire 22 through the lumen 16 and out through the proximal guidewire opening 17 (FIG. 4). The delivery catheter 200 is thus configured to be passed over the guidewire 22 in a rapid-exchange manner.

The pusher 6 tapers proximally inwardly at the opening 17 for a smooth crossing profile.

When assembled, the hypotube 5 and the pusher 6 are located substantially side-by-side (FIG. 4). This side-by-side assembly of the hypotube 5 relative to the pusher 6 enables the guidewire 22 to exit through the proximal guidewire opening 17 smoothly and substantially parallel to the longitudinal axis of the catheter 200 (FIG. 4). In particular the passage of the guidewire 22 through the proximal guidewire opening 17 does not increase the overall profile of the catheter 200.

A connector shaft 12 is fixed to the sheath 10 with the shaft 12 extending proximally over the pusher 6 towards the distal end of the hypotube 5, as illustrated in FIG. 1. The proximal end of the sheath 10 overlaps the distal end of the shaft 12, and a marker band 13 is located at the distal end of the shaft 12 between the shaft 12 and the sheath 10 (FIG. 7).

The actuator wire 9 extends distally through an actuator lumen 302 in the hypotube 5, out of the actuator lumen 302 at the distal end of the hypotube 5, externally along the pusher 6 to the proximal end of the shaft 12, as illustrated in FIG. 4. The wire 9 is attached to the exterior surface of the shaft 12, for example by bonding.

By attaching the wire 9 to the exterior of the shaft 12, this arrangement provides for more space within the pusher lumen 16 for guidewire passage.

In addition attachment of the actuator wire 9 to the exterior of the shaft 12 is an easier step to achieve from a manufacturing viewpoint than attachment to the interior of the relatively long shaft 12.

As illustrated in FIGS. 1 and 2, the restraining sheath 10 and the connector shaft 12 are movable in a sliding manner relative to the catheter body 2.

When the sheath 10 extends distally of a distal end of the spring pusher 6, the sheath 10 defines an internal reception space 11, as illustrated in FIGS. 5 to 7. A collapsed embolic protection filter 301 may be received within the reception space 11, where the filter 301 will be restrained by the sheath 10 in a low-profile configuration during delivery to a desired site in a vasculature. A suitable material for the sheath 10 is polyethyleneterephthalate (PET).

The distal end of the shaft 12 is flared outwardly (FIG. 7). During delivery of the filter 301, the distal end of the pusher 6 is spaced proximally of the distal end of the shaft 12, and the proximal end of an inner tubular member 306 of the filter 301 is partially inserted into the flared shaft 12, as illustrated in FIG. 7. This arrangement provides a bridge in stiffness between the relatively stiff shaft 12 and the relatively stiff inner tubular member 306 of the filter 301. Thus the possibility of buckling of the relatively flexible sheath 10 is minimised.

The distal end of the pusher 6 is engagable with the inner tubular member 306 of the filter 301 upon retraction of the sheath 10 to deploy the filter 301 out of the reception space 11.

As illustrated in FIG. 8, at the proximal end 3 of the catheter 200 a distal handle 8 is provided for gripping the catheter body 2 and a proximal handle 14 is provided for gripping the actuator wire 9. The distal handle 8 is injection moulded over the hypotube 5 and the proximal handle 14 is crimped to the proximal end of the wire 9.

The handles 8, 14 are movable relative to one another in a telescoping manner with the proximal handle 14 sliding within the distal handle 8. Movement of the handles 8, 14 is limited by means of stop means. Abutment of an outward annular protrusion 303 on the proximal handle 14 against the proximal end of the distal handle 8 prevents further movement of the proximal handle 14 distally relative to the distal handle 8. Engagement of a shoulder 304 on the proximal handle 14 with an inward annular protrusion 305 on the distal handle 8 prevents further movement of the proximal handle 14 proximally relative to the distal handle 8.

A releasable safety clip 307 is provided to maintain the handles 8, 14 fixed relative to one another.

When the catheter 200 is assembled the sheath 10 is directly connected to the proximal handle 14, and the pusher 6 is directly connected to the distal handle 8. Movement of the proximal handle 14 proximally relative to the distal handle 8 moves the wire 9, the connector shaft 12 and the sheath 10 proximally relative to the pusher 6 to facilitate deployment of the filter 301 from within the reception space 11.

The delivery catheter 200 may be used to deliver the embolic protection filter 301 through a vasculature and to deploy the embolic protection filter 301 downstream of a stenosed region in the vasculature to prevent potentially harmful emboli, which may be released into the blood stream during treatment of the stenosis, such as by a stenting procedure, from migrating further through the vascular system.

In use, a loading device 310 is partially inserted into the reception space 11 of the sheath 10. A pushing device 311 is then threaded through the tubular member 306 of the filter 301 and extended into the reception space 11, as illustrated in FIG. 9.

By moving the pushing device 311 proximally, an engagement stop 312 on the pushing device 311 engages the distal end of the tubular member 306 and the filter 301 is moved towards the loading device 310 (FIG. 10). Continued proximal movement of the pushing device 311 pushes the filter 301 through the loading device 310, thereby collapsing the filter 301, and into the reception space 11 (FIG. 11).

The catheter 200 with the collapsed filter 301 received within the reception space 11 are then moved together proximally away from the loading device 310 (FIG. 12).

The method of collapsing the filter 301 and loading the filter 301 into the reception space 11 is similar to that described in International patent application number PCT/IE01/00052, the relevant contents of which are incorporated herein by reference.

Next the guidewire 22 is inserted into a vasculature 315 and advanced through the vasculature 315 until the guidewire 22 has crossed a site of interest in the vasculature 315 (FIG. 13). A typical site of interest is a stenosed or diseased region 316 of the vasculature 315. The delivery catheter 200 is then threaded over the guidewire 22 by inserting the proximal end of the guidewire 22 into the guidewire lumen 16 at the distal end of the pusher 6, through the lumen 16, and out of the lumen 16 through the proximal guidewire opening 17. The catheter 200 is advanced over the guidewire 22 in a rapid-exchange manner until the reception space 11 is located downstream of the stenosis 316 (FIG. 14).

To deploy the filter 301 at the desired site in the vasculature 315 downstream of the stenosis 316, the proximal handle 14 is moved proximally while holding the distal handle 8 fixed, thereby causing the pull wire 9 and the connector shaft 12 to be pulled proximally, as illustrated in FIGS. 15 and 16. Because the connector shaft 12 is attached to the sheath 10, the sheath 10 also moves proximally while the pusher 6 does not move. In this way, the collapsed filter 301 is uncovered by the sheath 10 while the distal end of the pusher 6 abuts the proximal end of the tubular member 306 of the filter 301. The delivery catheter 200 thus enables the self-expanding filter 301 to expand outwardly to a deployed configuration. The distal end of the pusher 6 acts as an abutment for a controlled, accurate deployment of the filter 301 at the desired site in the vasculature 315.

When the filter 30 has been fully deployed at the desired site in the vasculature 315, the delivery catheter 200 is withdrawn from the vasculature 315 over the guidewire 22 in a rapid-exchange manner to leave the deployed filter 301 in place in the vasculature 315 (FIG. 17).

The movement of the elongate wire 9 proximally relative to the pusher 6 does not occlude the proximal guidewire opening 17, or in any way interfere with passage of the guidewire 22 through the guidewire lumen 16. Thus rapid exchange of the delivery catheter 200 over the guidewire 22 is possible during deployment of the filter 301 also.

During this deployment action, the connector shaft 12 slides proximally in a telescoping manner over the pusher 6. In this manner, the filter 301 may be accurately deployed in a controlled manner without the overall crossing profile of the delivery catheter 200 being adversely effected. In particular, no bulging or accordioning of the catheter 200 occurs during the deployment action.

The stainless steel pull wire 9 has a high tensile strength, and thus provides a stretch resistant link between the proximal pull handle 14 and the sheath 10 to facilitate accurate and recoil free deployment of the embolic protection filter 301 from within the reception space 11.

The hypotube 5 and the spring pusher 6 give the delivery catheter 200 excellent pushability and trackability for delivery through the vasculature 315, and provide extremely high compression resistance to significantly prevent compression, thereby enable a smooth and accurate deployment action.

When the delivery catheter 200 is used to deploy the embolic protection filter 301 in this manner, the non-moving elements of the catheter 200 are the distal handle 8, the hypotube 5, and the pusher 6. The moving elements of the catheter 200 are the proximal handle 14, the wire 9, the connector shaft 12, and the sheath 10.

The delivery catheter 200 of the invention facilitates accurate and intuitive filter deployment. By simply holding the distal handle 8 in a fixed position relative to the guide catheter and retracting the contoured proximal handle 14, the pull-wire 9 retracts the sheath 10 and the filter 301 is deployed.

The use of the internal pull wire 9 to connect the sheath 10 to the proximal handle 14 ensures that the filter 301 can be easily and accurately deployed in a precise location in a controlled, steady manner. In particular, the hypotube 5 and the distal handle 8 do not have to move relative to the guide catheter during the deployment action.

By attaching the pull-wire 9 to the connector shaft 12, this arrangement ensures that the tensile force is transmitted from the wire 9 to the shaft 12 proximally of the sheath 10. Thus the possibility of the sheath 10 being pulled to one side during wire retraction is minimised. Instead the sheath 10 slides smoothly in the longitudinal direction for accurate filter deployment.

It will be appreciated that the filter 301 may be deployed by any suitable movement of the sheath 10 proximally relative to the pusher 6. For example the pusher 6 may be advanced distally while maintaining the position of the sheath 10 fixed to deploy the filter 301 from within the reception space 11.

The rapid exchange delivery catheter of the invention facilitates the delivery of a bare wire filtration element over a standard length (180~190 cm) stepped guidewire.

Referring to FIGS. 18 to 22 there is illustrated another delivery catheter 1 according to the invention, which is similar to the delivery catheter 200 of FIGS. 1 to 17, and similar elements in FIGS. 18 to 22 are assigned the same reference numerals.

Figure 20:
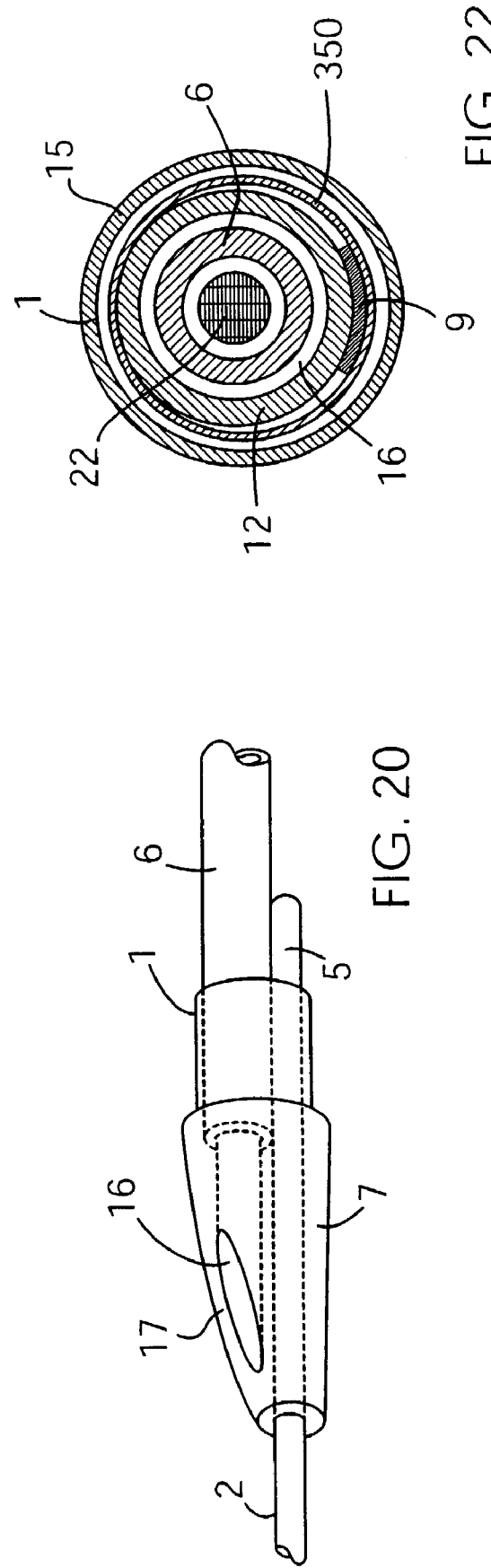
FIG. 20 is a perspective view of a part of the catheter of FIG. 18.

In this case the catheter 1 comprises an overmould junction piece 7 to connect the hypotube 5 to the spring pusher 6. The junction piece 7 is fixedly mounted to the hypotube 5 and the proximal end of the pusher 6 is fixedly attached to the junction piece 7 in a manner such that the hypotube 5 and the pusher 6 are located in a side-by-side overlapping arrangement, as illustrated in FIG. 20. The distal end of the hypotube 5 extends distally of the proximal end of the pusher 6, and distally of the junction piece 7 (FIG. 20) such that the hypotube 5 and the pusher 6 overlap.

The proximal guidewire opening 17 is provided in this case by an opening in the junction piece 7 aligned with the guidewire lumen 16 of the pusher 6. The hypotube 5 extends through the full length of the junction piece 7 (FIG. 20).

The junction piece 7 is stiffer than the hypotube 5, and thus assists in stabilising the compressive push force between the hypotube 5 and the spring pusher 6.

The junction piece 7 tapers proximally inwardly towards the hypotube 5 for a smooth crossing profile.

Figure 21:
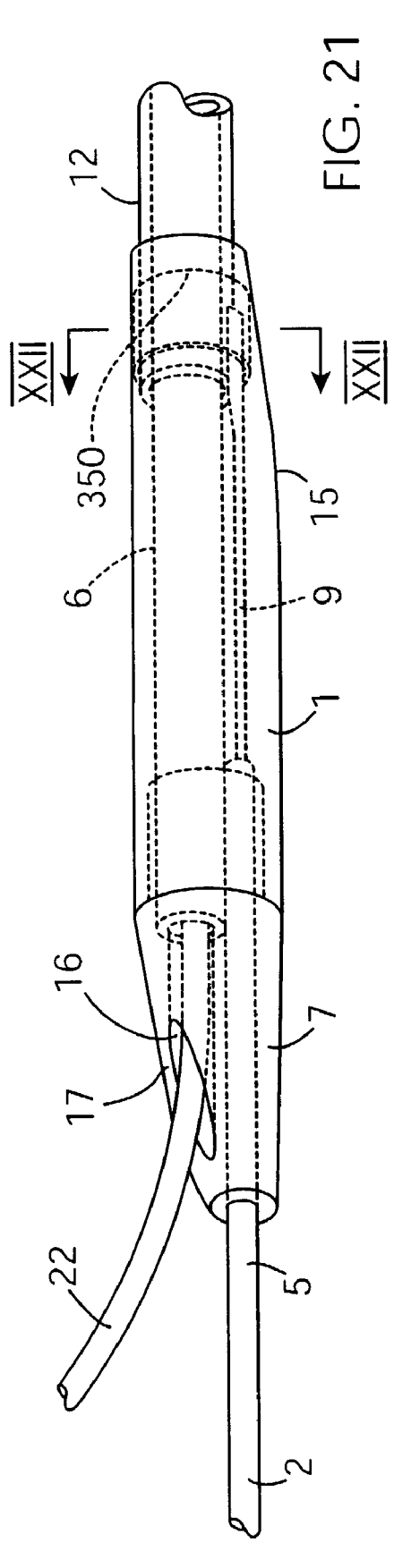
FIG. 21 is a perspective view of a part of the catheter of FIG. 18.
Figure 22:
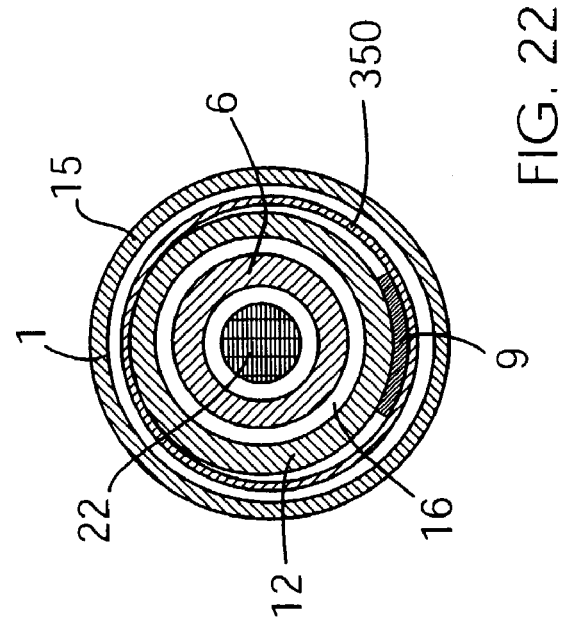
FIG. 22 is a view along line XXII-XXII in FIG. 21.

The actuator wire 9 is flattened down into a curved, dish configuration at the distal end of the wire 9, as illustrated in FIG. 22. The wire 9 is fixedly attached to the external surface of the connector shaft 12 by means of a heat shrink tubing 350 (FIG. 21).

The curved configuration of the wire 9 provides for a large area of contact between the wire 9 and the shaft 12 for a secure attachment of the wire 9 to the shaft 12.

The catheter 1 comprises a shielding sleeve 15 mounted to the junction piece 7. The sleeve 15 extends distally from the junction piece 7 over the wire 9 to a point distally of the heat shrink tubing 350 (FIG. 21). In this manner, the sleeve 15 acts to prevent snagging or interference with the wire 9, in particular during advancement of the deliver catheter 1 through the vasculature 315. The sleeve 15 also ensures the wire 9 follows the overall curvature of the catheter 1.

The connector shaft 12 is movable proximally relative to the sleeve 15 in a sliding, telescoping manner with the shaft 12 passing over the pusher 6 and through the interior of the sleeve 15, as illustrated in FIGS. 18 and 19.

The shielding sleeve 15 ensures the pull wire 9 follows the overall curvature of the catheter 1. Thus the wire 9 is prevented from following a straight line path upon retraction of the wire 9 when the catheter 1 is curved around a bend in a vasculature.

When the delivery catheter 1 is used to deploy the embolic protection filter 301 in this manner, the non-moving elements of the catheter 200 are the distal handle 8, the hypotube 5, the junction piece 7, the pusher 6, and the sleeve 15. The moving elements of the catheter 1 are the proximal handle 14, the wire 9, the connector shaft 12, and the sheath 10.

Figure 23:
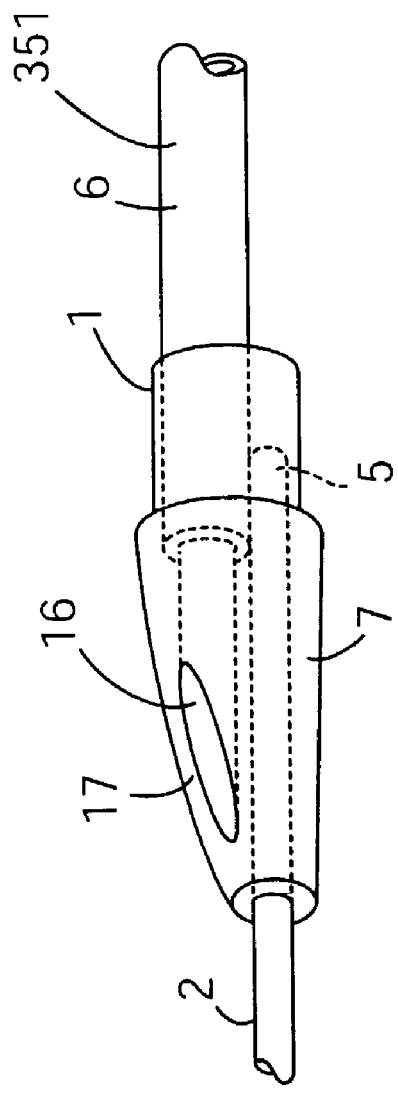
FIGS. 23 and 24 are perspective views of a part of other delivery catheters according to the invention.

In the delivery catheter 351 of FIG. 23, the hypotube 5 extends through only part of the junction piece 7. The distal end of the hypotube 5 is located distally of the proximal end of the pusher 6.

Figure 24:
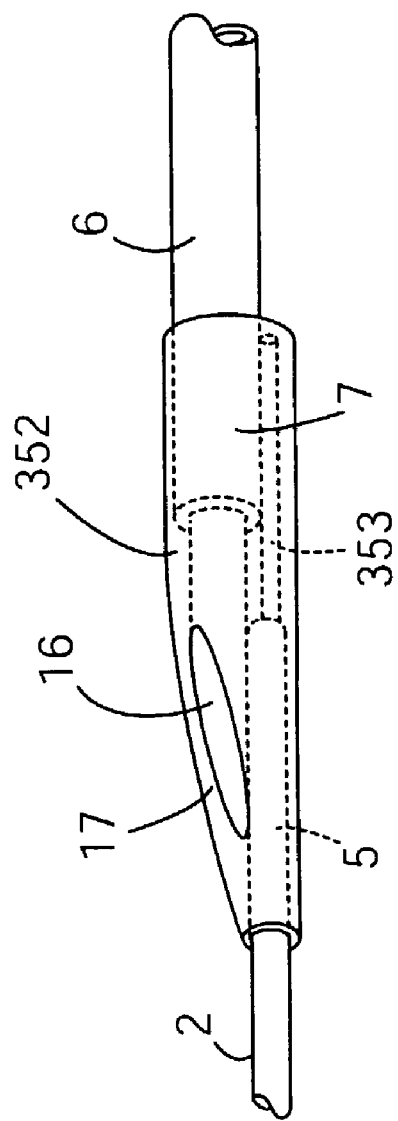
Figure 37:
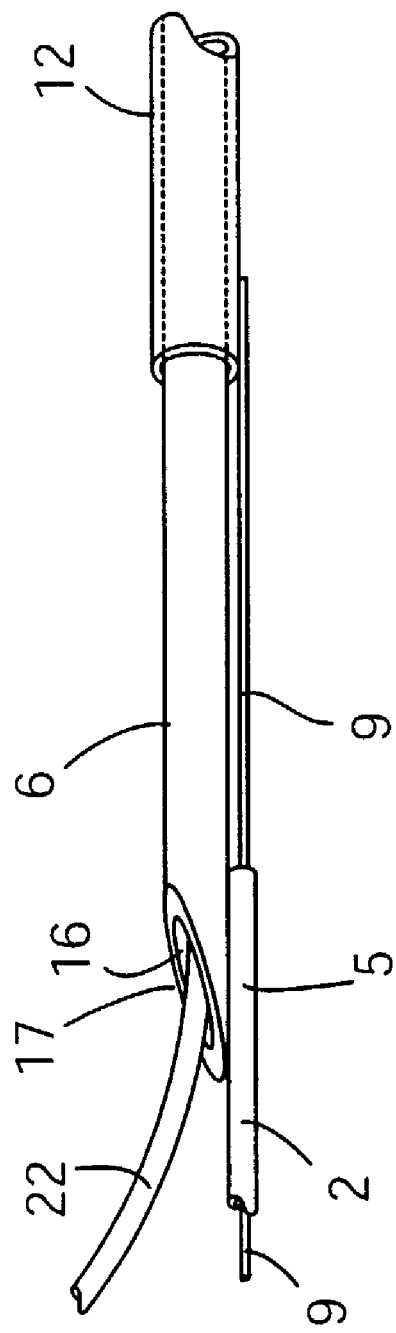
FIG. 37 is a partially cut-away, perspective view of a part of the catheter of FIG. 1.

In the delivery catheter 352 of FIG. 24, the hypotube 5 and the pusher 6 do not overlap. The distal end of the hypotube 5 is located proximally of the proximal end of the pusher 6. An actuator lumen 353 is provided through the junction piece 7 aligned with the actuator lumen 302 of the hypotube 5 for passage of the actuator wire 9 through the hypotube 5 and through the junction piece 7 to the connector shaft 12.

Referring to FIG. 25 there is illustrated a further delivery catheter 360 according to the invention, which is similar to the delivery catheter 200 of FIGS. 1 to 17, and similar elements in FIG. 25 are assigned the same reference numerals.

The catheter 360 comprises the shielding sleeve 15 fixedly mounted to the pusher 6 and the hypotube 5. The sleeve 15 extends distally of the proximal guidewire opening 17.

The pusher 6 is directly attached to the hypotube 5 in a side-by-side overlapping arrangement with the proximal end of the pusher 6 located proximally of the distal end of the hypotube 5.

In FIG. 26 there is illustrated another delivery catheter 370 according to the invention, which is similar to the delivery catheter 360 of FIG. 25, and similar elements in FIG. 26 are assigned the same reference numerals.

In the catheter 370 the sleeve 15 also extends proximally of the proximal guidewire opening 17. The sleeve 15 tapers proximally inwardly towards the hypotube 5.

The proximal guidewire opening 17 is provided by an opening in the sleeve 15 aligned with the guidewire lumen 16 of the pusher 6.

FIG. 27 illustrates another delivery catheter 380 according to the invention, which is similar to the delivery catheter 370 of FIG. 26, and similar elements in FIG. 27 are assigned the same reference numerals.

In this case the shielding sleeve and the connector shaft are provided by a single integral sleeve 381 slidably mounted to the hypotube 5 and the pusher 6, and extending from a point proximally of the proximal guidewire opening 17 to the sheath 10, to which the sleeve 381 is fixed.

The actuator wire 9 extends through the actuator lumen 302 of the hypotube 5, out of the distal end of the hypotube 5, internally through the sleeve 381, out of the sleeve 381 through an opening 382 in the sidewall of the sleeve 381, externally along the sleeve 381 to a point of attachment of the wire 9 to the sleeve 381.

Retraction of the wire 9 relative to the hypotube 5 causes the entire sleeve 381, and the sheath 10 to move proximally over the pusher 6 in a sliding manner for deployment of the filter 301 from within the reception space 11.

It will be appreciated that the actuator wire 9 may be fixedly attached to the connector shaft 12 by a variety of different means within the scope of the invention in suit.

For example the distal end of the wire 9 may be fixedly attached to the external surface of the shaft 12 in a simple side-by-side arrangement, as illustrated in FIG. 28, in a manner similar to that described previously with reference to FIGS. 1 to 17.

Alternatively the distal end of the wire 9 may be flattened down into a curved dish configuration, as illustrated in FIG. 29, in a manner similar to that described previously with reference to FIGS. 18 to 22. The curved configuration of the wire 9 provides for a large area of contact between the wire 9 and the external surface of the shaft 12 for a secure attachment of the wire 9 to the external surface of the shaft 12.

As a further alternative the wire 9 may be fixedly attached to the external surface of the shaft 12 by means of a heat shrink tubing 350, as illustrated in FIG. 30, in a manner similar to that described previously with reference to FIGS. 18 to 22.

In another case the actuator wire 9 may divide into two or more legs 390, 391 after exiting the actuator lumen 302 of the hypotube 5. The legs 390, 391 are fixedly attached to the external surface of the shaft 12 on opposite sides of the shaft 12, as illustrated in FIG. 31, to ensure a balanced retraction of the shaft 12 over the pusher 6.

As another alternative the distal end of the actuator wire 9 may be fixedly attached to the internal surface of the connector shaft 12, as illustrated in FIG. 32. The proximal end of the shaft 12 may be flared outwardly to accommodate passage of the wire 9 into the shaft 12.

In a further case the distal end of the actuator wire 9 may be fixedly attached to the connector shaft 12 by embedding the distal end of the wire 9 within the wall of the shaft 12, as illustrated in FIGS. 33 and 34.

As a further alternative the connector shaft 400 may comprise one or more reinforcement elements 401 extending longitudinally along the shaft 400. The actuator wire 9 may be fixedly attached to one of the reinforcement elements 401. In the case where the reinforcement element 401 is a wire, the actuator wire 9 may be integrally formed with the reinforcement wire 401, as illustrated in FIGS. 35 and 36, for a secure connection between the actuator wire 9 and the connector shaft 400.

Figure 38:
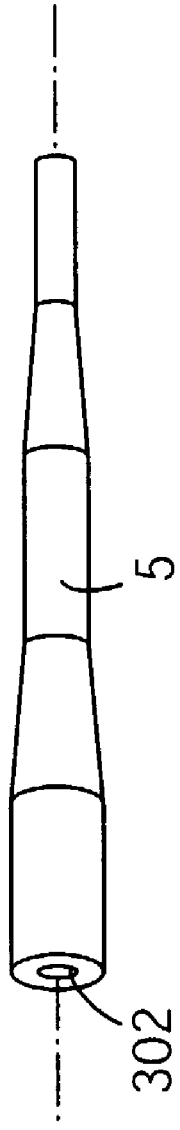
FIG. 38 is a perspective view of a catheter shaft part of another delivery catheter according to the invention.

The cross-sectional area of the hypotube 5 may vary along the length of the hypotube 5. A particularly preferred arrangement is for the hypotube 5 to taper distally inwardly, as illustrated in FIG. 38.

The larger cross-sectional area towards the proximal end of the hypotube 5 results in greater stiffness towards the proximal end of the hypotube 5 for enhanced pushability of the delivery catheter. The smaller cross-sectional area towards the distal end of the hypotube 5 results in greater flexibility towards the distal end of the hypotube 5 for enhanced trackability of the delivery catheter.

Figure 39:
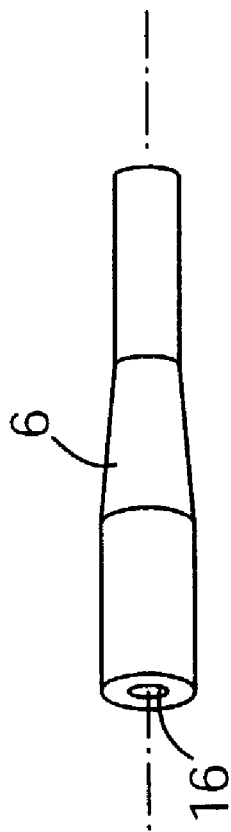

The cross-sectional area of the spring pusher 6 may also vary along the length of the pusher 6. A particularly preferred arrangement is for the pusher 6 to taper distally inwardly, as illustrated in FIG. 39, for similar reasons to those discussed previously with reference to FIG. 38.

It is not essential that the proximal portion 5 of the catheter body 2 be formed from a hypotube. The proximal portion 5 may alternatively be formed from a polymeric material with a sufficiently large modulus of elasticity to provide the required pushability for the catheter. Suitable polymeric materials include PEEK, PA, and polyamide. Another alternative is for the proximal portion 5 to be formed from a coiled spring. A lining of polytetrafluoroethylene or of fluoroethylenepolymer may be provided along the proximal portion 5 for improved wire movement.

The distal pusher 6 of the catheter body 2 may be formed from a close coiled metal spring 410, as illustrated in FIG. 40, and as described previously with reference to FIGS. 1 to 17. The close coiled spring 410 provides the combination of good pushability and good flexibility. A polymer jacket 411 may be provided around the interior surface of the coiled spring 410, as illustrated in FIG. 41, for ease of guidewire passage through the coiled spring 410.

Alternatively the distal pusher 6 of the catheter body 2 may be formed from a polymeric material as illustrated in FIG. 42, with a sufficiently large modulus of elasticity to provide the required pushability. A lining 412 of polytetrafluoroethylene or of fluoroethylenepolymer may be provided along the pusher 6, as illustrated in FIG. 43, for improved wire movement.

One or more axial reinforcing wires 413 may be provided extending along the pusher 6, as illustrated in FIG. 44, to increase the compressive modulus of the pusher 6 without reducing the flexibility of the pusher 6.

The connector shaft 12 may be formed from a polymeric material, as illustrated in FIG. 45, with a sufficiently large modulus of elasticity to ensure the shaft 12 is smoothly and accurately retracted. A lining 412 of polytetrafluoroethylene or of fluoroethylenepolymer may be provided along the shaft 12, as illustrated in FIG. 46, for ease of movement of the shaft 12 relative to the pusher 6.

One or more axial reinforcing wires 413 may be provided extending along the shaft 12, as illustrated in FIG. 47, to increase the tensile modulus of the shaft 12 without reducing the flexibility of the shaft 12.

The actuator 9 may be of a metal, such as stainless steel, or Nitinol, or alternatively may be of a fibre, such as Kevlar. The cross-section of the actuator 9 may be round (FIG. 48), or square (FIG. 49), or rectangular (FIG. 50), or flattened down into a curve (FIG. 51) in a manner similar to that described previously with reference to FIGS. 18 to 22, or star-shaped (FIG. 52). The actuator 9 may comprise two or more wire elements fixed together, as illustrated in FIG. 53. The wire elements may be braided together over the full length of the actuator 9 (FIG. 54), or over only part of the length of the actuator 9 with the wire elements splaying apart distally (FIG. 55).

Referring to FIGS. 56 and 57 there is illustrated another delivery catheter 430 according to the invention, which is similar to the delivery catheter 200 of FIGS. 1 to 17, and similar elements in FIGS. 56 and 57 are assigned the same reference numerals.

In this case the pusher 6 comprises a proximal tubular portion 432 with a distally extending arm 431. An abutment half-ring 433 is provided at the distal end of the arm 431 for engaging the tubular member 306 of the embolic protection filter 434 in the reception space 11 upon retraction of the distal sheath 10 (FIG. 57).

The guidewire 22 extends in a side-by-side manner relative to the distal arm 431, through the guidewire lumen 16 of the proximal tubular portion 432 of the pusher 6, and out through the proximal guidewire opening 17.

The filter 434 of FIGS. 56 and 57 is of a different configuration to the filter 301 described previously with reference to FIGS. 1 to 17. The filter 434 has a single proximally extending support leg 435.

It will be appreciated that the delivery catheter of the invention in suit is suitable for delivering and deploying at a desired site in a vasculature a variety of embolic protection filters. The delivery catheter is particularly suitable for delivering and deploying a filter which is independent of and slidable relative to the guidewire 22.

In FIGS. 57(*a*) to 57(*c*) there is illustrated another delivery catheter 600 according to the invention, which is similar to the delivery catheter 200 of FIGS. 1 to 17, and similar elements in FIGS. 57(*a*) to 57(*c*) are assigned the same reference numerals.

In this case the distal end of the shaft 12 is not flared outwardly, and the proximal end of the inner tubular member 306 is not inserted into the shaft 12, during delivery of the embolic protection filter 610.

Instead a bridging sleeve 601 is provided mounted around the shaft 12 distally of the marker band 13, as illustrated in FIG. 57(*c*). The sleeve 601 extends distally of the distal end of the shaft 12, such that the proximal end of the inner tubular member 306 of the filter 610 may be partially inserted into the sleeve 601 during delivery of the filter 610 (FIG. 57(*c*)). This arrangement provides a bridge in stiffness between the relatively stiff shaft 12 and the relatively stiff inner tubular member 306 of the filter 610. Thus the possibility of buckling of the relatively flexible sheath 10 is minimised.

It is noted that the filter 610 of FIGS. 57(*a*) to 57(*c*) is of a different configuration to the filter 301 described previously with reference to FIGS. 1 to 17. In particular the inner tubular member 306 of the filter 610 does not have any step formations or protrusions at the proximal end of the inner tubular member 306 (FIG. 57(*c*)).

The delivery catheter of the invention is also suitable for over-the-wire exchange over a guidewire. The rapid exchange configuration is not essential.

FIGS. 58 and 59 illustrate another delivery catheter 440 according to the invention, which is similar to the delivery catheter 200 of FIGS. 1 to 17, and similar elements in FIGS. 58 and 59 are assigned the same reference numerals.

The catheter 440 is configured for over-the-wire exchange over the guidewire 22. The pusher 6 extends proximally in a side-by-side manner relative to the hypotube 5 (FIG. 59) to the distal handle 8 to which both the pusher 6 and the hypotube 5 are fixed. The proximal guidewire opening 17 is provided at a proximal end of the distal handle 8 (FIG. 58).

The catheter body 2 may alternatively be provided in the form of a single catheter shaft 451 with the guidewire lumen 16 and the actuator lumen 302 extending therethrough, as illustrated in the delivery catheter 450 of FIG. 60.

FIG. 61 illustrates another delivery catheter 20 according to the invention, which is similar to the delivery catheter 200 of FIGS. 1 to 17, and similar elements in FIG. 61 are assigned the same reference numerals.

In this case, there is no junction piece provided between the hypotube 5 and the spring pusher 6. Instead the distal end of the hypotube 5 is fixed directly, for example by means of bonding to the proximal end of the spring pusher 6. The proximal guidewire opening 17 is provided at the proximal end of the spring pusher 6.

In addition, the catheter 20 has no shielding sleeve around the pull wire 9. In this case, the wire 9 is uncovered between the distal end of the hypotube 5 and the exterior point of attachment 21 to the connector shaft 12.

As illustrated in FIG. 61, the hypotube 5 is radially offset from the spring pusher 6, such that the proximal guidewire opening 17 is substantially in-line with the guidewire lumen 16 through the pusher 6. This arrangement enables the guidewire 22 to pass through the lumen 16 in a substantially unobstructed manner, and thus enables quick and easy exchange of the delivery catheter 20 over the guidewire 22.

In FIG. 62 there is illustrated another delivery catheter 30 according to the invention, which is similar to the delivery catheter 20 of FIG. 61, and similar elements in FIG. 62 are assigned the same reference numerals.

In this case, the hypotube 5, the junction piece 7 and the spring pusher are substantially aligned. The pull wire 9 exits the hypotube 5 through a sidewall opening 31 in the sidewall of the hypotube 5 and then extends distally to the point of attachment 21 to the connector shaft 12. The proximal guidewire opening 17 in the junction piece 7 is also provided in the form of a sidewall opening in the sidewall of the junction piece 7. The guidewire 22 exits the guidewire lumen 16 in the spring pusher 6 through the sidewall opening 17.

As illustrated in FIG. 62, the pull wire opening 31 is located proximally of the guidewire opening 17. By locating the guidewire opening 17 close to the distal end of the catheter 30, this provides a user with enhanced control of the guidewire 22.

It will be appreciated however that the pull wire opening may alternatively be located distally of the guidewire opening, or substantially adjacent to the guidewire opening.

In the delivery catheter 30 of FIG. 62, the connector shaft 12 extends a substantial distance proximally over the pusher 6 towards the pull wire opening 31. However it is not essential for the connector shaft 12 to extend proximally over the full length of the pusher 6. In the delivery catheter 40 of FIG. 63, the connector shaft 12 extends proximally over only a portion of the length of the pusher 6.

The catheter 40 also comprises an annular ring 41 at the distal end of the pusher 6 for abutting the embolic protection filter 301 in the reception space 11 upon retraction of the sheath 10 relative to the pusher 6.

Referring now to FIG. 64, there is illustrated another delivery catheter 55 according to the invention, which is similar to the delivery catheter 40 of FIG. 63, and similar elements in FIG. 64 are assigned the same reference numerals.

The catheter body 2 comprises, in this case, a unitary hypotube 50 extending from the proximal end of the catheter body 2 to the sheath 10.

The delivery catheter 55 comprises two wires 51 extending distally through the hypotube 50 from the proximal handle 14 through two separate, parallel actuator lumena 53. The wires 51 exit the lumena 53 through two wire openings 31 and extend to the proximal end of the sheath 10 to which the wires 51 are directly attached. In particular, there is no proximally extending connector shaft provided in this case.

By the use of two parallel pull wires 51, this ensures that the sheath retraction will proceed in a balanced manner.

Both the proximal guidewire opening 17 and the two wire openings 31 are provided by openings in the sidewall of the unitary hypotube 50.

As illustrated in FIG. 64, the guidewire opening 17 is located proximally of the two wire openings 31. By locating the wire openings 31 distally of the guidewire opening 17, this minimises the possibility of the wires 51 becoming tangled or damaged between the openings 31 and the sheath 10.

The actuator wires 9 may extend through two separate actuator lumena in the hypotube 5 (FIG. 66) or alternatively may both extend through a single actuator lumen (FIG. 67).

As another alternative a single actuator wire 9 may be provided extending through the actuator lumen of the hypotube 5 (FIG. 68), or alternatively three or more actuator wires 9 may all extend through the single actuator lumen (FIG. 69).

As the actuator wires 9 extend distally from the wire openings 31 in the hypotube 5 to the shaft 12, the wires 9 pass externally along the hypotube 5, as illustrated in FIG. 70. The hypotube 5 may alternatively be formed into a substantially oblong cross-section, as illustrated in FIG. 71, to minimise the overall crossing profile of the delivery catheter.

The actuator wire 9 is fixedly attached to the external surface of the shaft 12 at opposite sides of the shaft 12, as illustrated in FIG. 72. This arrangement ensures that sheath retraction proceeds in a balanced manner.

FIGS. 73 and 74 illustrate a further delivery catheter 460 according to the invention, which is similar to the delivery catheter 30 of FIG. 62, and similar elements in FIGS. 73 and 74 are assigned the same reference numerals.

In this case the pusher 6 is directly attached to the hypotube 5 without any junction piece 7. The pusher 6 is aligned with the hypotube 5 for passage of the guidewire 22 from the guidewire lumen 16 of the pusher 6 out through the proximal guidewire opening 17.

The pusher 6 has a smaller diameter than the hypotube 5 such that the external surface of the pusher 6 is stepped inwardly of the external surface of the hypotube 5. In this way the actuator wire 9 may pass distally from the actuator lumen 302 of the hypotube 5 substantially parallel to the longitudinal axis of the catheter 460 towards the connector shaft 12. This arrangement ensures the overall crossing profile of the catheter 460 is not increased at the exit of the wire 9 from the actuator lumen 302.

This arrangement of stepping back the pusher 6 from the hypotube 5 may also be used when the catheter comprises two actuator wires 9 (FIG. 75), three actuator wires 9 (FIG. 76), or more actuator wires 9 extending through the hypotube 5.

In the delivery catheter 470 of FIG. 77, the proximal portion 5 of the catheter body 2 and the pusher 6 are provided by a unitary catheter shaft 471 extending from the proximal end of the catheter 470 to the sheath 10.

FIG. 78 illustrates a further delivery catheter 60 according to the invention, which is similar to the delivery catheter 55 of FIG. 64, and similar elements in FIG. 78 are assigned the same reference numerals.

The catheter 60 has a single pull wire 61 extending distally through the hypotube 50 from the proximal handle 14 through a wire lumen 53. The wire 61 exits the lumen 53 through the sidewall opening 31. At the exit opening 31, the wire 61 divides into two parallel distal wire portions 62 which extend distally to the proximal end of the sheath 10 to which the distal wire portions 62 are directly attached.

In FIG. 79 there is illustrated another delivery catheter 70 according to the invention, which is similar to the delivery catheter 30 of FIG. 62, and similar elements in FIG. 79 are assigned the same reference numerals.

There is no proximally extending connector shaft provided in this case. The pull wire 9 extends distally to the sheath 10, where the wire 9 is directly attached to the exterior surface of the sheath at the point of attachment 21.

The catheter 70 comprises an outer tube 71 mounted co-axially around the hypotube 5 and the wire 9 between the proximal guidewire opening 17 and the point of attachment 21. As illustrated in FIG. 79, the wire 9 extends between the pusher 6 and the outer tube 71.

By extending the wire 9 through the outer tube 71, this arrangement prevents looping of the relatively long section of wire 9 between the wire opening 31 and the point of attachment 21, upon pulling of the wire 9 proximally to retract the sheath 10 and deploy the embolic protection filter 301 from within the reception space 11.

The outer tube 71 is fixedly attached to the pusher 6, for example by means of heat shrinking the tube 71 to the pusher 6. A suitable material for the outer tube 71 is a hypotube material.

As illustrated in the catheter 80 of FIG. 80, two or more pull wires 81 may be provided extending distally between the pusher 6 and the outer tube 71. Using two or more pull wires 81 may result in a more balanced retraction of the sheath 10.

It will be appreciated that a pull wire may be configured to extend distally from the proximal end of the catheter body 2 externally along the full length of the catheter body 2 to the sheath 10. In such a case, the outer tube 71 will be particularly useful in channelling the wire distally to the sheath 10, and in preventing looping of the wire when the wire is retracted to deploy the embolic protection filter 301 from within the reception space 11.

Figure 81:
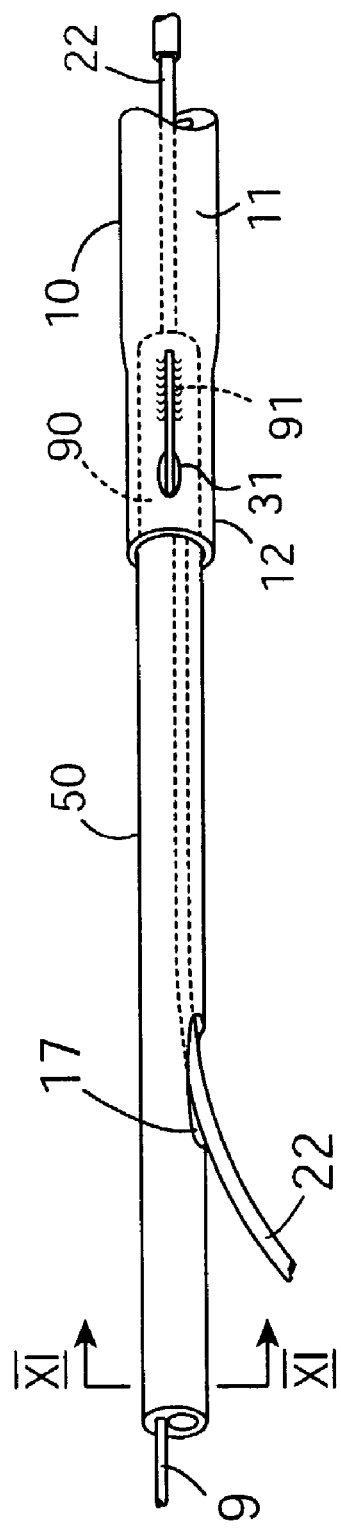
Figure 82:
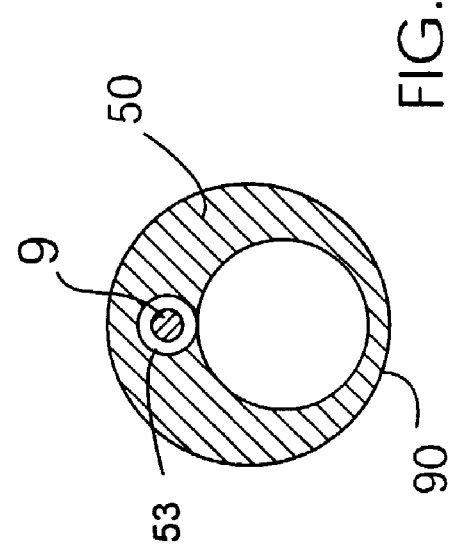
FIG. 82 is a view along line XI-XI in FIG. 81.

Referring next to FIGS. 81 and 82, there is illustrated a further delivery catheter 90 according to the invention, which is similar to the delivery catheter 55 of FIG. 64, and similar elements in FIGS. 81 and 82 are assigned the same reference numerals.

In this case, the wire opening 31 is located distally of the proximal guidewire opening 17. The connector shaft 12 extends proximally over the hypotube 50 passed the wire opening 31, and the wire 9 is attached to the interior surface of the shaft 12 at the point of attachment 91.

As illustrated in FIG. 81, the wire 9 extends distally from the proximal handle 14 through the lumen 53 in the hypotube 50, out of this lumen 53 through the wire opening 31 in the sidewall of the hypotube 50, and then along the hypotube 50 to the point of attachment 91.

The wire 9 facilitates movement of the sheath 10 proximally relative to the hypotube 50, and in this manner enables deployment of the embolic protection filter 301 from within the reception space 11.

The sheath 10 is retractable relative to the hypotube 50 in a sliding manner by pulling the wire 9 proximally relative to the hypotube 50. The distal end of the hypotube 50 provides a distal abutment surface for engagement with the embolic protection filter 301 in the reception space 11 upon retraction of the sheath 10. This abutment ensures that deployment of the embolic protection filter 301 at a desired site may be accurately controlled by the user by manipulating the proximal handle 14 and the distal handle 8 from externally of the vasculature.

The stiffness of the catheter body 2 may decrease distally in a gradual manner. Ideally the stiffness decrease occurs across the proximal guidewire opening 17 in the sidewall of the hypotube 50. This non-discrete stiffness reduction ensures the catheter body 2 does not have any points of weakness. The stiffness reduction may in one case be achieved by providing a stiffer section of hypotube fixed to a more flexible spring coil section.

Figure 83:
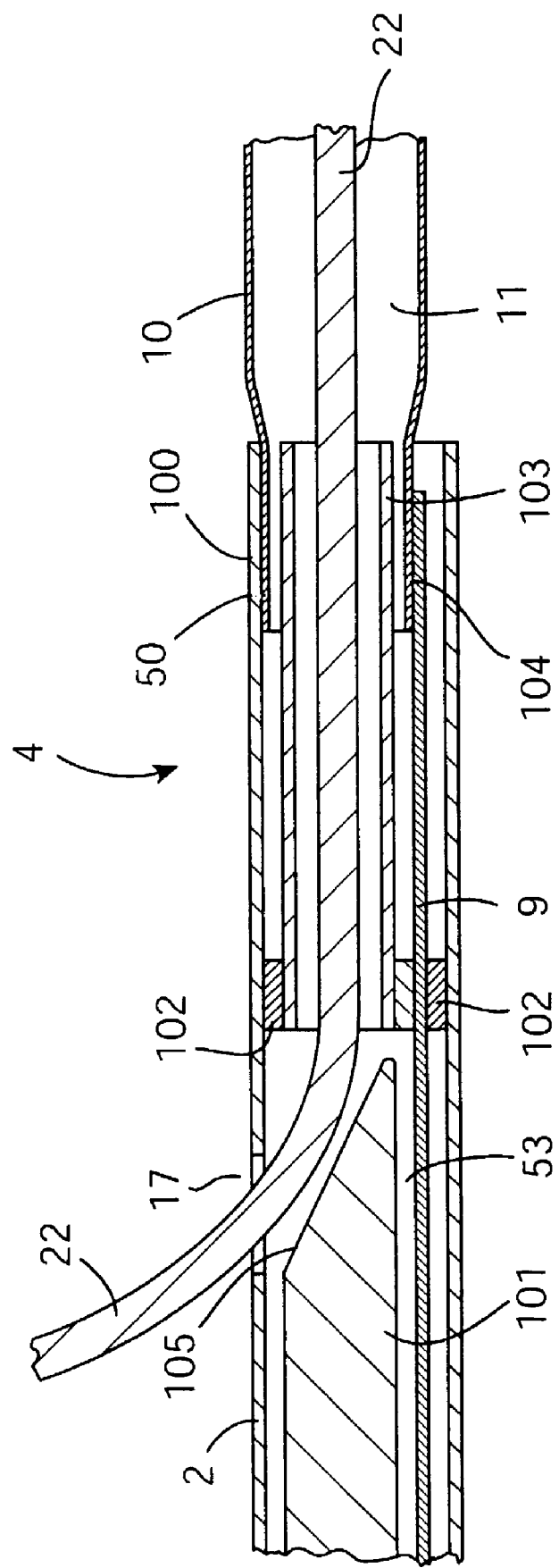
FIG. 83 is a cross-sectional, side view of another delivery catheter according to the invention passing over a guidewire.
Figure 84:
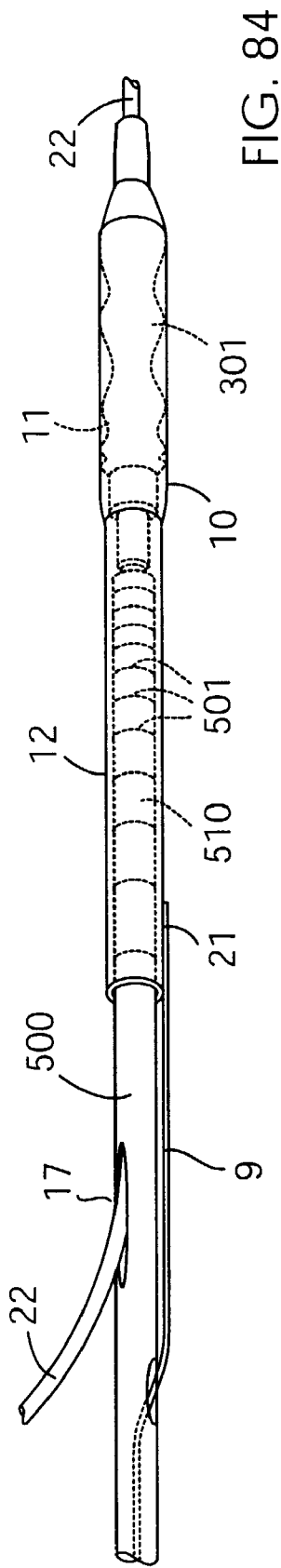
FIG. 84 is a partially cut-away, perspective view of a further delivery catheter according to the invention passing over a guidewire.

In FIG. 83 there is illustrated another delivery catheter 100 according to the invention, which is similar to the delivery catheter 55 of FIG. 64, and similar elements in FIG. 83 are assigned the same reference numerals.

The catheter 100 comprises an inner tube 103 mounted co-axially within the hypotube 50 distally of the proximal guidewire opening 17. The inner tube 103 is fixedly attached to the interior surface of the hypotube 50 by means of an annular ring 102.

The sheath 10 is mounted at the distal end 4 of the catheter body 2 between the inner tube 103 and the hypotube 50. Upon retraction of the sheath 10, the sheath 10 is slidable proximally in a telescoping manner relative to the hypotube 50 and the inner tube 103.

The wire 9, in this case, extends distally from the proximal handle 14 through the wire lumen 53 along the full length of the catheter body 2 to the sheath 10. The wire 9 is fixedly attached to the exterior surface of the sheath 10 at the point of attachment 104.

A reinforcement support in the form of a skived tube 101 is provided extending proximally of the guidewire opening 17 through the hypotube 50. The sloping distal end face 105 of the tube 101 assists in guiding the guidewire 22 from the inner tube 103 out through the guidewire opening 17.

Upon retraction of the wire 9 relative to the hypotube 50, the sheath 10 moves proximally relative to the hypotube 50 and the inner tube 103 sliding between the hypotube 50 and the inner tube 103 in a telescoping manner. Abutment of the inner tube 103 with the embolic protection filter 301 within the reception space 11 facilitates controlled deployment of the filter 301 at a desired site in the vasculature.

Figure 85:
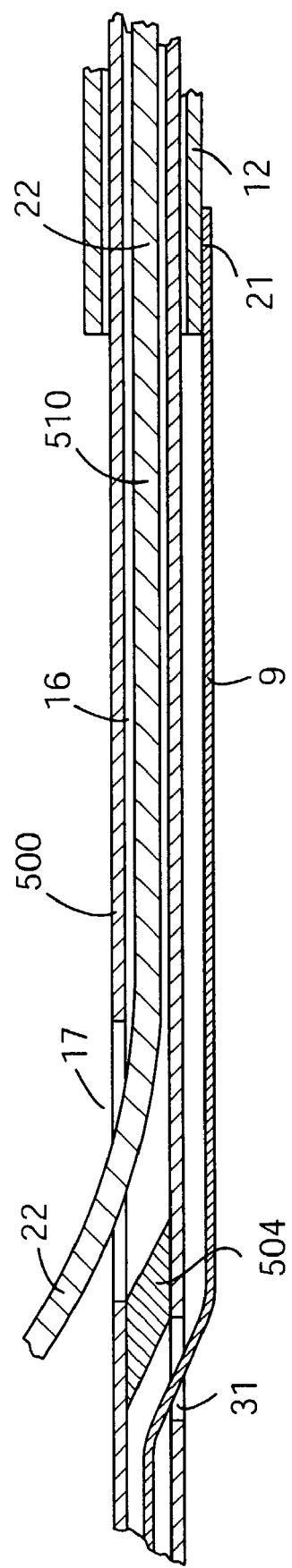
FIG. 85 is an enlarged, cross-sectional, side view of a part of the catheter of FIG. 84.

FIGS. 85 and 86 illustrate another delivery catheter 510 according to the invention, which is similar to the delivery catheter 30 of FIG. 62, and similar elements in FIGS. 85 and 86 are assigned the same reference numerals.

The catheter body 500 is of one-piece construction with a variable pitch spiral 501 cut along the catheter body 500 for enhanced trackability. The spacings between the spiral 501 decreases distally. In this way the trackability of the catheter 510 increases distally.

The proximal guidewire opening 17 and the actuator wire opening 31 are provided in the catheter body 500 by laser drilling for passage of the guidewire 22 and the elongate actuator wire 9, from externally of the catheter body 500 into the catheter body 500, or from internally of the catheter body 500 out of the catheter body 500. A ramp 504 is provided to guide passage of the guidewire 22 or the elongate actuator wire 9 through the openings 17, 31.

Frictional losses during deployment of an embolic protection filter using the delivery catheter of the invention are low.

The delivery catheter according to the invention is particularly suitable for delivering an embolic protection filter in a downstream direction to a desired location in a vasculature, and deploying the filter at the desired location.

The invention is not limited to the embodiments hereinbefore described, with reference to the accompanying drawings, which may be varied in construction and detail.

The invention claimed is:

1. A delivery catheter system comprising:
    a guidewire,
    an embolic protection filter comprising a tubular member for receiving the guidewire, and
    a delivery catheter,
    the delivery catheter comprising a catheter shaft, an engagement element and an operating element, the catheter shaft defining a proximal end, a distal end and a control lumen for the operating element;
    the engagement element is attached to and extends distally from the catheter shaft, the engagement element comprising a proximal end, a distal end and a distal region adjacent the distal end;

a pod defining a reception space for the filter, the pod being slidable relative to the engagement element over the distal region of the engagement element upon operation of the operating element to facilitate deployment of the filter from within the reception space, the pod having a proximal end and a distal end; and the engagement element is adapted for engaging the filter in the reception space upon sliding of the pod proximally relative to the engagement element;

wherein the engagement element defines a guidewire lumen therethrough for passage of the guidewire, the guidewire lumen being separate from the control lumen, the engagement element and the filter are not attached to and can move independently of the guidewire, the engagement element is slidable relative to the filter, the pod and the operating element, the guidewire is separate from the operating element, and the engagement element is adapted to slide completely within the pod, such that the distal end of the engagement element is proximal of the distal end of the pod.

2. A catheter system as claimed in claim 1 wherein a distal end of the catheter shaft is disconnected from a proximal end of the pod for movement of the pod relative to the catheter shaft.

3. A catheter system as claimed in claim 2 wherein the distal end of the catheter shaft is spaced proximally of the proximal end of the pod.

4. A catheter system as claimed in claim 3 wherein the catheter comprises a covering sleeve extending between the distal end of the catheter shaft and the proximal end of the pod.

5. A catheter system as claimed in claim 4 wherein the covering sleeve is mounted to the catheter shaft.

6. A catheter system as claimed in claim 5 wherein the pod is movable relative to the covering sleeve.

7. A catheter system as claimed in claim 4 wherein the covering sleeve is mounted to the pod.

8. A catheter system as claimed in claim 7 wherein the covering sleeve is movable relative to the catheter shaft.

9. A catheter system as claimed in claim 1 wherein the engagement element comprises a pusher.

10. A catheter system as claimed in claim 9 wherein the pusher comprises a coiled spring.

11. A catheter system as claimed in claim 9 wherein the pusher is of a high modulus of elasticity polymeric material.

12. A catheter system as claimed in claim 1 wherein the engagement element has a guidewire opening at a proximal end of the guidewire lumen.

13. A catheter system as claimed in claim 12 wherein the engagement element is configured for passage of a guidewire from the guidewire lumen through the guidewire opening substantially parallel to the longitudinal axis of the catheter shaft.

14. A catheter system as claimed in claim 13 wherein the longitudinal axis of the engagement element is substantially parallel to the longitudinal axis of the catheter shaft at least in the region of the guidewire opening.

15. A catheter system as claimed in claim 12 wherein the guidewire opening faces proximally.

16. A catheter system as claimed in claim 12 wherein the guidewire opening is located a substantial distance distally of a proximal end of the catheter for rapid exchange of the catheter over a guidewire.

17. A catheter system as claimed in claim 1 wherein the cross-sectional area of the operating element is small relative to the cross-sectional area of the catheter shaft along at least part of the length of the operating element.

18. A catheter system as claimed in claim 17 wherein the cross-sectional area of the operating element is small relative to the cross-sectional area of the catheter shaft in the region of a guidewire opening at a proximal end of the engagement element.

19. A claim system as claimed in claim 18 wherein the cross-sectional area of the operating element is small relative to the cross-sectional area of the catheter shaft for a distance of at least 10 mm proximally of the guidewire opening.

20. A catheter system as claimed in claim 19 wherein the cross-sectional area of the operating element is small relative to the cross-sectional area of the catheter shaft for a distance of at least 20 mm proximally of the guidewire opening.

21. A catheter system as claimed in claim 20 wherein the cross-sectional area of the operating element is small relative to the cross sectional area of the catheter shaft for a distance of at least 30 mm proximally of the guidewire opening.

22. A catheter system as claimed in claim 21 wherein the cross sectional area of the operating element is small relative to the cross-sectional area of the catheter shaft for a distance of at least 40 mm proximally of the guidewire opening.

23. A catheter system as claimed in claim 1 wherein the diameter of the operating element is in the range of from 0.008" to 0.015".

24. A catheter system as claimed in claim 23 wherein the diameter of the operating element is in the range of from 0.01" to 0.012".

25. A catheter system as claimed in claim 1 wherein the operating element comprises a control wire.

26. A catheter system as claimed in claim 25 wherein the operating element comprises a pull wire.

27. A catheter system as claimed in claim 1 wherein an operating element exits the control lumen at a location distally of a guidewire opening at a proximal end of the engagement element.

28. A catheter system as claimed in claim 1 wherein the operating element exits the control lumen at a location proximally of the guidewire opening.

29. A catheter system as claimed in claim 1 wherein the operating element exits the control lumen at a location adjacent the guidewire opening.

30. A catheter system as claimed in claim 1 wherein the catheter comprises means to guide passage of a guidewire through the guidewire opening.

31. A catheter system as claimed in claim 30 wherein the means to guide passage comprises a guide tube.

32. A catheter system as claimed in claim 31 wherein the guide tube is located at the guidewire opening.

33. A catheter system as claimed in claim 31 wherein the guide tube is mounted to the engagement element.

34. A catheter system as claimed in claim 1 wherein the guidewire lumen of the engagement element is offset radially from the control lumen of the catheter shaft.

35. A catheter system as claimed in claim 1 wherein the catheter shaft comprises a mounting piece for attaching the engagement element to the catheter shaft.

36. A catheter system as claimed in claim 35 wherein the mounting piece is more flexible than the catheter shaft and the engagement element.

37. A catheter system as claimed in claim 35 wherein the mounting piece is more stiff than the catheter shaft and the engagement element.

38. A catheter system as claimed in claim 35 wherein the mounting piece tapers proximally inwardly.

39. A catheter system as claimed in claim 35 wherein the mounting piece tapers distally inwardly.

40. A catheter system as claimed in claim 35 wherein the guidewire opening is provided by an opening in the mounting piece.

41. A catheter system as claimed in claim 1 wherein the distal end of the catheter shaft is located distally of the proximal end of the engagement element.

42. A catheter system as claimed in claim 1 wherein the engagement element comprises an engagement surface for engaging the filter in the reception space.

43. A catheter system as claimed in claim 42 wherein the engagement surface is provided by a distal end face of the engagement element.

44. A catheter system as claimed in claim 42 wherein the engagement surface extends circumferentially around the engagement element to define an "O"-shape.

45. A catheter system as claimed in claim 42 wherein the engagement surface extends partially circumferentially around the engagement element to define an "U"-shape.

46. A catheter system as claimed in claim 42 wherein the engagement surface is configured to engage the tubular member of the filter.

47. A catheter system as claimed in claim 1 wherein the operating element is attached to the pod.

48. A catheter system as claimed in claim 47 wherein the operating element is attached to an exterior surface of the pod.

49. A catheter system as claimed in claim 1 wherein the pod comprises a proximal portion and a distal portion, the distal portion defining the reception space.

50. A catheter system as claimed in claim 49 wherein the operating element is attached to the proximal portion.

51. A catheter system as claimed in claim 49 wherein the proximal portion and the distal portion are fixed together by means of a marker band.

52. A catheter system as claimed in claim 1 wherein the operating element is a control wire.

53. A catheter system as claimed in claim 52 wherein the operating element is a pull wire.

54. A catheter system as claimed in claim 52 wherein the operating element comprises a plurality of wires.

55. A catheter system as claimed in claim 54 wherein the wires are braided together along at least part of the length of the operating element.

56. A catheter system as claimed in claim 1 wherein the stiffness of the catheter shaft decreases distally.

57. A catheter system as claimed in claim 56 wherein the stiffness of the catheter shaft decreases from a point proximally of the guidewire opening to a point distally of the guidewire opening.

58. A catheter system as claimed in claim 56 wherein the stiffness decreases in a gradual manner.

59. A catheter system as claimed in claim 56 wherein the catheter shaft includes at least one slot in the catheter shaft.

60. A catheter system as claimed in claim 59 wherein the slot extends along the catheter shaft in a spiral.

61. A catheter system as claimed in claim 60 wherein the pitch of the spiral varies along the catheter shaft.

62. A catheter system as claimed in claim 1 wherein the pod is thin-walled.

63. A catheter system as claimed in claim 62 wherein the pod has a wall thickness in the range of from 0.0005" to 0.00075".

64. A catheter system as claimed in any of claims 1 to 8, 9 to 11, 12 to 46, 47 to 63 wherein the pod is of the material polyethyleneterephthalate or polytetrafluoroethylene.

* * * * *